(12) United States Patent
Schaller et al.

(10) Patent No.: US 8,535,327 B2
(45) Date of Patent: Sep. 17, 2013

(54) DELIVERY APPARATUS FOR USE WITH IMPLANTABLE MEDICAL DEVICES

(75) Inventors: Laurent B. Schaller, Los Altos, CA (US); David S. Needleman, San Carlos, CA (US); James K. Lee, San Mateo, CA (US); Jeffrey L. Emery, Emerald Hills, CA (US)

(73) Assignee: Benvenue Medical, Inc., Santa Clara, CA (US)

( * ) Notice: Subject to any disclaimer, the term of this patent is extended or adjusted under 35 U.S.C. 154(b) by 642 days.

(21) Appl. No.: 12/724,858

(22) Filed: Mar. 16, 2010

(65) Prior Publication Data

US 2010/0241177 A1 Sep. 23, 2010

Related U.S. Application Data

(60) Provisional application No. 61/160,882, filed on Mar. 17, 2009.

(51) Int. Cl.
*A61B 17/70* (2006.01)
*A61F 2/44* (2006.01)

(52) U.S. Cl.
USPC .......................................... 606/99; 623/17.16

(58) Field of Classification Search
USPC .... 606/86 A, 86 R, 99–10; 623/17.11–17.16
See application file for complete search history.

(56) References Cited

U.S. PATENT DOCUMENTS

| 1,965,653 | A | 7/1934 | Kennedy |
| 3,091,237 | A | 5/1963 | Skinner |
| 3,112,743 | A | 12/1963 | Cochran et al. |
| 3,648,294 | A | 3/1972 | Shahrestani |
| 3,800,788 | A | 4/1974 | White |
| 3,875,595 | A | 4/1975 | Froning |
| 3,889,665 | A | 6/1975 | Ling et al. |
| 3,964,480 | A | 6/1976 | Froning |
| 4,262,676 | A | 4/1981 | Jamshidi |
| 4,274,163 | A | 6/1981 | Malcom et al. |
| 4,312,337 | A | 1/1982 | Donohue |
| 4,313,434 | A | 2/1982 | Segal |
| 4,399,814 | A | 8/1983 | Pratt, Jr. et al. |
| 4,462,394 | A | 7/1984 | Jacobs |
| 4,466,435 | A | 8/1984 | Murray |
| 4,467,479 | A | 8/1984 | Brody |
| 4,488,549 | A | 12/1984 | Lee et al. |
| 4,562,598 | A | 1/1986 | Kranz |
| 4,595,006 | A | 6/1986 | Burke et al. |

(Continued)

FOREIGN PATENT DOCUMENTS

| DE | 19710392 C1 | 7/1999 |
| DE | 202006005868 | 6/2006 |

(Continued)

*Primary Examiner* — Matthew Lawson
(74) *Attorney, Agent, or Firm* — Cook Alex, Ltd.

(57) ABSTRACT

An apparatus for delivering an intravertebral implant into a vertebral body of a vertebra. The apparatus includes a cannula operatively connected to a housing wherein the cannula is adapted for insertion into the vertebral body. The housing includes a drive system for advancing a guide member through the cannula, out of a distal end opening of the cannula and into the vertebral body. Further, the drive system also selectively or simultaneously advances a pushing element that is adapted to push an intravertebral implant along the guide member so that the guide member guides the implant through the cannula, out of the distal end opening of the cannula and into the vertebral body for implantation.

24 Claims, 20 Drawing Sheets

(56) References Cited

U.S. PATENT DOCUMENTS

| | | |
|---|---|---|
| 4,625,722 A | 12/1986 | Murray |
| 4,627,434 A | 12/1986 | Murray |
| 4,628,945 A | 12/1986 | Johnson, Jr. |
| 4,630,616 A | 12/1986 | Tretinyak |
| 4,665,906 A | 5/1987 | Jervis |
| 4,686,973 A | 8/1987 | Frisch |
| 4,697,584 A | 10/1987 | Haynes |
| 4,706,670 A | 11/1987 | Andersen et al. |
| 4,714,478 A | 12/1987 | Fischer |
| 4,743,256 A | 5/1988 | Brantigan |
| 4,772,287 A | 9/1988 | Ray et al. |
| 4,834,069 A | 5/1989 | Umeda |
| 4,838,282 A | 6/1989 | Strasser et al. |
| 4,863,476 A | 9/1989 | Shepperd |
| 4,878,915 A | 11/1989 | Brantigan |
| 4,888,022 A | 12/1989 | Huebsch |
| 4,888,024 A | 12/1989 | Powlan |
| 4,892,550 A | 1/1990 | Huebsch |
| 4,896,662 A | 1/1990 | Noble |
| 4,941,466 A | 7/1990 | Romano |
| 4,961,740 A | 10/1990 | Ray et al. |
| 4,969,888 A | 11/1990 | Scholten et al. |
| 5,015,247 A | 5/1991 | Michelson |
| 5,015,255 A | 5/1991 | Kuslich |
| 5,051,189 A | 9/1991 | Farrah |
| 5,053,035 A | 10/1991 | McLaren |
| 5,055,104 A | 10/1991 | Ray |
| 5,059,193 A | 10/1991 | Kuslich |
| 5,071,435 A | 12/1991 | Fuchs et al. |
| 5,098,435 A | 3/1992 | Stednitz et al. |
| 5,102,413 A | 4/1992 | Poddar |
| 5,108,404 A | 4/1992 | Scholten et al. |
| 5,122,130 A | 6/1992 | Keller |
| 5,123,926 A | 6/1992 | Pisharodi |
| 5,147,366 A | 9/1992 | Arroyo et al. |
| 5,163,989 A | 11/1992 | Campbell et al. |
| 5,171,280 A | 12/1992 | Baumgartner |
| 5,176,683 A | 1/1993 | Kimsey et al. |
| 5,176,692 A | 1/1993 | Wilk et al. |
| 5,183,052 A | 2/1993 | Terwilliger |
| 5,192,327 A | 3/1993 | Brantigan |
| 5,242,879 A | 9/1993 | Abe et al. |
| 5,257,632 A | 11/1993 | Turkel et al. |
| 5,263,953 A | 11/1993 | Bagby |
| 5,303,718 A | 4/1994 | Krajicek |
| 5,306,308 A | 4/1994 | Gross et al. |
| 5,306,310 A | 4/1994 | Siebels |
| 5,322,505 A | 6/1994 | Krause et al. |
| 5,330,429 A | 7/1994 | Noguchi et al. |
| 5,331,975 A | 7/1994 | Bonutti |
| 5,361,752 A | 11/1994 | Moll et al. |
| 5,383,932 A | 1/1995 | Wilson et al. |
| 5,385,151 A | 1/1995 | Scarfone et al. |
| 5,423,816 A | 6/1995 | Lin |
| 5,423,817 A | 6/1995 | Lin |
| 5,423,850 A | 6/1995 | Berger |
| 5,431,658 A | 7/1995 | Moskovich |
| 5,441,538 A | 8/1995 | Bonutti |
| 5,454,365 A | 10/1995 | Bonutti |
| 5,454,827 A | 10/1995 | Aust et al. |
| 5,462,563 A | 10/1995 | Shearer et al. |
| 5,468,245 A | 11/1995 | Vargas, III |
| 5,480,400 A | 1/1996 | Berger |
| 5,484,437 A | 1/1996 | Michelson |
| 5,509,923 A | 4/1996 | Middleman et al. |
| 5,514,143 A | 5/1996 | Bonutti et al. |
| 5,514,153 A | 5/1996 | Bonutti |
| 5,522,398 A | 6/1996 | Goldenberg et al. |
| 5,522,790 A | 6/1996 | Moll et al. |
| 5,522,846 A | 6/1996 | Bonutti |
| 5,527,343 A | 6/1996 | Bonutti |
| 5,527,624 A | 6/1996 | Higgins et al. |
| 5,531,856 A | 7/1996 | Moll et al. |
| 5,534,023 A | 7/1996 | Henley |
| 5,538,009 A | 7/1996 | Byrne et al. |
| 5,540,711 A | 7/1996 | Kieturakis et al. |
| 5,545,222 A | 8/1996 | Bonutti |
| 5,549,679 A | 8/1996 | Kuslich |
| 5,562,736 A | 10/1996 | Ray et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,593,409 A | 1/1997 | Michelson |
| 5,601,556 A | 2/1997 | Pisharodi |
| 5,601,572 A | 2/1997 | Middleman et al. |
| 5,632,746 A | 5/1997 | Middleman et al. |
| 5,645,597 A | 7/1997 | Krapiva |
| 5,665,122 A | 9/1997 | Kambin |
| 5,669,926 A | 9/1997 | Aust et al. |
| 5,674,295 A | 10/1997 | Ray et al. |
| 5,681,263 A | 10/1997 | Flesch |
| 5,693,100 A | 12/1997 | Pisharodi |
| 5,695,513 A | 12/1997 | Johnson et al. |
| 5,700,239 A | 12/1997 | Yoon |
| 5,702,453 A | 12/1997 | Rabbe et al. |
| 5,702,454 A | 12/1997 | Baumgartner |
| 5,716,416 A | 2/1998 | Lin |
| 5,741,253 A | 4/1998 | Michelson |
| 5,749,879 A | 5/1998 | Middleman et al. |
| 5,755,797 A | 5/1998 | Baumgartner |
| 5,772,661 A | 6/1998 | Michelson |
| 5,782,832 A | 7/1998 | Larsen et al. |
| 5,788,703 A | 8/1998 | Mittelmeier et al. |
| 5,807,275 A | 9/1998 | Jamshidi |
| 5,820,628 A | 10/1998 | Middleman et al. |
| 5,823,979 A | 10/1998 | Mezo |
| 5,824,093 A | 10/1998 | Ray et al. |
| 5,827,289 A | 10/1998 | Reiley et al. |
| 5,836,948 A | 11/1998 | Zucherman et al. |
| 5,851,212 A | 12/1998 | Zirps et al. |
| 5,860,977 A | 1/1999 | Zucherman et al. |
| 5,865,848 A | 2/1999 | Baker |
| 5,904,690 A | 5/1999 | Middleman et al. |
| 5,919,235 A | 7/1999 | Husson et al. |
| 5,925,074 A | 7/1999 | Gingras et al. |
| 5,961,554 A | 10/1999 | Janson et al. |
| 5,972,015 A | 10/1999 | Scribner et al. |
| 5,976,186 A | 11/1999 | Bao et al. |
| 5,980,522 A | 11/1999 | Koros et al. |
| 6,015,436 A | 1/2000 | Schonhoffer |
| 6,019,793 A | 2/2000 | Perren et al. |
| 6,030,401 A | 2/2000 | Marino |
| 6,033,406 A | 3/2000 | Mathews |
| 6,033,412 A | 3/2000 | Losken et al. |
| 6,039,740 A | 3/2000 | Olerud |
| 6,045,552 A | 4/2000 | Zucherman et al. |
| 6,048,342 A | 4/2000 | Zucherman et al. |
| 6,048,346 A | 4/2000 | Reiley et al. |
| 6,048,360 A | 4/2000 | Khosravi et al. |
| 6,066,154 A | 5/2000 | Reiley et al. |
| 6,068,630 A | 5/2000 | Zucherman et al. |
| 6,083,225 A | 7/2000 | Winslow et al. |
| 6,090,143 A | 7/2000 | Meriwether et al. |
| 6,102,950 A | 8/2000 | Vaccaro |
| 6,110,210 A | 8/2000 | Norton et al. |
| 6,113,640 A | 9/2000 | Tormala et al. |
| 6,119,044 A | 9/2000 | Kuzma |
| 6,123,705 A | 9/2000 | Michelson |
| 6,126,660 A | 10/2000 | Dietz |
| 6,127,597 A | 10/2000 | Beyar et al. |
| 6,159,211 A | 12/2000 | Boriani et al. |
| 6,159,244 A | 12/2000 | Suddaby |
| 6,165,218 A | 12/2000 | Husson et al. |
| 6,174,337 B1 | 1/2001 | Keenan |
| 6,179,873 B1 | 1/2001 | Zientek |
| 6,187,048 B1 | 2/2001 | Milner et al. |
| 6,190,414 B1 | 2/2001 | Young et al. |
| 6,193,757 B1 | 2/2001 | Foley et al. |
| 6,197,033 B1 | 3/2001 | Haid, Jr. et al. |
| D439,980 S | 4/2001 | Reiley et al. |
| 6,217,579 B1 | 4/2001 | Koros |
| 6,221,082 B1 | 4/2001 | Marino et al. |
| 6,224,603 B1 | 5/2001 | Marino |

| Patent No. | Date | Inventor |
|---|---|---|
| 6,235,030 B1 | 5/2001 | Zucherman et al. |
| 6,235,043 B1 | 5/2001 | Reiley et al. |
| 6,238,491 B1 | 5/2001 | Davidson et al. |
| 6,241,734 B1 | 6/2001 | Scribner et al. |
| 6,248,110 B1 | 6/2001 | Reiley et al. |
| 6,251,140 B1 | 6/2001 | Marino et al. |
| 6,261,289 B1 | 7/2001 | Levy |
| 6,264,695 B1 | 7/2001 | Stoy |
| 6,267,763 B1 | 7/2001 | Castro |
| 6,280,456 B1 | 8/2001 | Scribner et al. |
| 6,280,475 B1 | 8/2001 | Bao et al. |
| 6,290,724 B1 | 9/2001 | Marino |
| D449,691 S | 10/2001 | Reiley et al. |
| 6,296,647 B1 | 10/2001 | Robioneck et al. |
| 6,312,443 B1 | 11/2001 | Stone |
| 6,364,828 B1 | 4/2002 | Yeung et al. |
| 6,368,325 B1 | 4/2002 | McKinley et al. |
| 6,387,130 B1 | 5/2002 | Stone et al. |
| 6,402,750 B1 | 6/2002 | Atkinson et al. |
| 6,419,705 B1 | 7/2002 | Erickson |
| 6,423,071 B1 | 7/2002 | Lawson |
| 6,423,083 B2 | 7/2002 | Reiley et al. |
| 6,423,089 B1 | 7/2002 | Gingras et al. |
| 6,425,919 B1 | 7/2002 | Lambrecht |
| 6,428,541 B1 | 8/2002 | Boyd et al. |
| 6,436,140 B1 | 8/2002 | Liu et al. |
| 6,440,138 B1 | 8/2002 | Reiley et al. |
| 6,451,019 B1 | 9/2002 | Zucherman et al. |
| 6,468,279 B1 | 10/2002 | Reo |
| 6,478,805 B1 | 11/2002 | Marino et al. |
| 6,482,235 B1 | 11/2002 | Lambrecht et al. |
| 6,485,518 B1 | 11/2002 | Cornwall et al. |
| D467,657 S | 12/2002 | Scribner |
| 6,488,710 B2 | 12/2002 | Besselink |
| 6,491,626 B1 | 12/2002 | Stone et al. |
| 6,491,695 B1 | 12/2002 | Roggenbuck |
| 6,498,421 B1 | 12/2002 | Oh et al. |
| 6,500,178 B2 | 12/2002 | Zucherman et al. |
| 6,500,205 B1 | 12/2002 | Michelson |
| 6,508,839 B1 | 1/2003 | Lambrecht et al. |
| 6,511,471 B2 | 1/2003 | Rosenman et al. |
| 6,512,958 B1 | 1/2003 | Swoyer et al. |
| D469,871 S | 2/2003 | Sand |
| 6,520,991 B2 | 2/2003 | Huene |
| D472,323 S | 3/2003 | Sand |
| 6,530,930 B1 | 3/2003 | Marino et al. |
| 6,533,791 B1 | 3/2003 | Betz et al. |
| 6,533,797 B1 | 3/2003 | Stone et al. |
| 6,540,747 B1 | 4/2003 | Marino |
| 6,554,833 B2 | 4/2003 | Levy et al. |
| 6,558,390 B2 | 5/2003 | Cragg |
| 6,562,074 B2 | 5/2003 | Gerbec et al. |
| 6,575,919 B1 | 6/2003 | Reiley et al. |
| 6,575,979 B1 | 6/2003 | Cragg |
| 6,576,016 B1 | 6/2003 | Hochshuler et al. |
| 6,579,291 B1 | 6/2003 | Keith et al. |
| 6,582,431 B1 | 6/2003 | Ray |
| 6,582,433 B2 | 6/2003 | Yun |
| 6,595,998 B2 | 7/2003 | Johnson et al. |
| 6,602,293 B1 | 8/2003 | Biermann et al. |
| 6,607,544 B1 | 8/2003 | Boucher et al. |
| 6,610,094 B2 | 8/2003 | Husson |
| 6,613,054 B2 | 9/2003 | Scribner et al. |
| 6,620,196 B1 | 9/2003 | Trieu |
| 6,623,505 B2 | 9/2003 | Scribner et al. |
| D482,787 S | 11/2003 | Reiss |
| 6,641,587 B2 | 11/2003 | Scribner et al. |
| 6,645,213 B2 | 11/2003 | Sand et al. |
| 6,648,917 B2 | 11/2003 | Gerbec et al. |
| D483,495 S | 12/2003 | Sand |
| 6,656,178 B1 | 12/2003 | Veldhuizen et al. |
| 6,656,180 B2 | 12/2003 | Stahurski |
| 6,660,037 B1 | 12/2003 | Husson et al. |
| 6,663,647 B2 | 12/2003 | Reiley et al. |
| 6,666,890 B2 | 12/2003 | Michelson |
| 6,666,891 B2 | 12/2003 | Boehm, Jr. et al. |
| 6,676,663 B2 | 1/2004 | Higueras et al. |
| 6,676,665 B2 | 1/2004 | Foley et al. |
| 6,682,561 B2 | 1/2004 | Songer et al. |
| 6,685,742 B1 | 2/2004 | Jackson |
| 6,689,125 B1 | 2/2004 | Keith et al. |
| 6,689,168 B2 | 2/2004 | Lieberman |
| 6,692,563 B2 | 2/2004 | Zimmermann |
| 6,706,070 B1 | 3/2004 | Wagner et al. |
| 6,716,216 B1 | 4/2004 | Boucher et al. |
| 6,716,247 B2 | 4/2004 | Michelson |
| 6,716,957 B2 | 4/2004 | Tunc |
| 6,719,761 B1 | 4/2004 | Reiley et al. |
| 6,719,773 B1 | 4/2004 | Boucher et al. |
| 6,723,128 B2 | 4/2004 | Uk |
| 6,726,691 B2 | 4/2004 | Osorio et al. |
| D490,159 S | 5/2004 | Sand |
| 6,740,093 B2 | 5/2004 | Hochschuler et al. |
| D492,032 S | 6/2004 | Muller et al. |
| 6,755,841 B2 | 6/2004 | Fraser et al. |
| D492,775 S | 7/2004 | Doelling et al. |
| D493,533 S | 7/2004 | Blain |
| 6,758,673 B2 | 7/2004 | Fromovich et al. |
| 6,764,514 B1 | 7/2004 | Li et al. |
| D495,417 S | 8/2004 | Doelling et al. |
| 6,773,460 B2 | 8/2004 | Jackson |
| 6,783,530 B1 | 8/2004 | Levy |
| 6,793,679 B2 | 9/2004 | Michelson |
| 6,796,983 B1 | 9/2004 | Zucherman et al. |
| 6,805,695 B2 | 10/2004 | Keith et al. |
| 6,808,537 B2 | 10/2004 | Michelson |
| 6,814,736 B2 | 11/2004 | Reiley et al. |
| 6,814,756 B1 | 11/2004 | Michelson |
| 6,821,298 B1 | 11/2004 | Jackson |
| 6,830,589 B2 | 12/2004 | Erickson |
| 6,835,205 B2 | 12/2004 | Atkinson et al. |
| 6,835,206 B2 | 12/2004 | Jackson |
| 6,840,944 B2 | 1/2005 | Suddaby |
| 6,852,126 B2 | 2/2005 | Ahlgren |
| 6,852,129 B2 | 2/2005 | Gerbec et al. |
| 6,863,668 B2 | 3/2005 | Gillespie et al. |
| 6,863,672 B2 | 3/2005 | Reiley et al. |
| 6,863,673 B2 | 3/2005 | Gerbec et al. |
| 6,866,682 B1 | 3/2005 | An et al. |
| 6,881,228 B2 | 4/2005 | Zdeblick et al. |
| 6,883,520 B2 | 4/2005 | Lambrecht et al. |
| 6,887,248 B2 | 5/2005 | McKinley et al. |
| 6,893,466 B2 | 5/2005 | Trieu |
| 6,899,716 B2 | 5/2005 | Cragg |
| 6,899,719 B2 | 5/2005 | Reiley et al. |
| D506,828 S | 6/2005 | Layne et al. |
| 6,905,512 B2 | 6/2005 | Paes et al. |
| 6,908,506 B2 | 6/2005 | Zimmermann |
| 6,921,403 B2 | 7/2005 | Cragg et al. |
| 6,923,810 B1 | 8/2005 | Michelson |
| 6,923,813 B2 | 8/2005 | Phillips et al. |
| 6,923,814 B2 | 8/2005 | Hildebrand et al. |
| 6,929,647 B2 | 8/2005 | Cohen |
| 6,945,973 B2 | 9/2005 | Bray |
| 6,952,129 B2 | 10/2005 | Lin et al. |
| 6,962,606 B2 | 11/2005 | Michelson |
| 6,964,674 B1 | 11/2005 | Matsuura et al. |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,008,453 B1 | 3/2006 | Michelson |
| 7,014,633 B2 | 3/2006 | Cragg |
| 7,018,089 B2 | 3/2006 | Wenz et al. |
| 7,018,415 B1 | 3/2006 | McKay |
| 7,018,453 B2 | 3/2006 | Klein et al. |
| 7,029,498 B2 | 4/2006 | Boehm et al. |
| 7,044,954 B2 | 5/2006 | Reiley et al. |
| 7,063,703 B2 | 6/2006 | Reo |
| 7,066,961 B2 | 6/2006 | Michelson |
| 7,069,087 B2 | 6/2006 | Sharkey et al. |
| 7,070,598 B2 | 7/2006 | Lim et al. |
| 7,074,226 B2 | 7/2006 | Roehm, III et al. |
| 7,081,120 B2 | 7/2006 | Li et al. |
| 7,081,122 B1 | 7/2006 | Reiley et al. |

| Patent/Publication | Date | Name |
|---|---|---|
| 7,087,055 B2 | 8/2006 | Lim et al. |
| 7,094,257 B2 | 8/2006 | Mujwid et al. |
| 7,115,128 B2 | 10/2006 | Michelson |
| 7,115,163 B2 | 10/2006 | Zimmermann |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,128,760 B2 | 10/2006 | Michelson |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| 7,156,874 B2 | 1/2007 | Paponneau et al. |
| 7,156,875 B2 | 1/2007 | Michelson |
| 7,166,107 B2 | 1/2007 | Anderson |
| 7,179,293 B2 | 2/2007 | McKay |
| 7,189,242 B2 | 3/2007 | Boyd et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,220,281 B2 | 5/2007 | Lambrecht et al. |
| 7,223,227 B2 | 5/2007 | Pflueger |
| 7,226,481 B2 | 6/2007 | Kuslich |
| 7,241,297 B2 | 7/2007 | Shaolian et al. |
| 7,244,273 B2 | 7/2007 | Pedersen et al. |
| 7,250,060 B2 | 7/2007 | Trieu |
| 7,252,671 B2 | 8/2007 | Scribner et al. |
| 7,267,687 B2 | 9/2007 | McGuckin, Jr. |
| 7,270,679 B2 | 9/2007 | Istephanous et al. |
| 7,311,713 B2 | 12/2007 | Johnson et al. |
| 7,316,714 B2 | 1/2008 | Gordon et al. |
| 7,318,840 B2 | 1/2008 | McKay |
| 7,320,689 B2 | 1/2008 | Keller |
| 7,322,962 B2 | 1/2008 | Forrest |
| 7,383,639 B2 | 6/2008 | Malandain |
| 7,485,134 B2 | 2/2009 | Simonson |
| 2001/0011174 A1 | 8/2001 | Reiley et al. |
| 2001/0016741 A1 | 8/2001 | Burkus et al. |
| 2002/0016583 A1 | 2/2002 | Cragg |
| 2002/0026195 A1 | 2/2002 | Layne et al. |
| 2002/0026244 A1 | 2/2002 | Trieu |
| 2002/0045942 A1 | 4/2002 | Ham |
| 2002/0068974 A1 | 6/2002 | Kuslich et al. |
| 2002/0082608 A1 | 6/2002 | Reiley et al. |
| 2002/0087163 A1 | 7/2002 | Dixon et al. |
| 2002/0091390 A1 | 7/2002 | Michelson |
| 2002/0099385 A1 | 7/2002 | Ralph et al. |
| 2002/0107519 A1 | 8/2002 | Dixon et al. |
| 2002/0107573 A1 | 8/2002 | Steinberg |
| 2002/0156482 A1 | 10/2002 | Scribner et al. |
| 2002/0169471 A1 | 11/2002 | Ferdinand |
| 2002/0172851 A1 | 11/2002 | Corey et al. |
| 2002/0173796 A1 | 11/2002 | Cragg |
| 2002/0173851 A1 | 11/2002 | McKay |
| 2002/0183761 A1 | 12/2002 | Johnson et al. |
| 2002/0183778 A1 | 12/2002 | Reiley et al. |
| 2002/0191487 A1 | 12/2002 | Sand |
| 2003/0018390 A1 | 1/2003 | Husson |
| 2003/0032963 A1 | 2/2003 | Reiss et al. |
| 2003/0050644 A1 | 3/2003 | Boucher et al. |
| 2003/0074075 A1 | 4/2003 | Thomas, Jr. et al. |
| 2003/0108588 A1 | 6/2003 | Chen et al. |
| 2003/0130664 A1 | 7/2003 | Boucher et al. |
| 2003/0171812 A1 | 9/2003 | Grunberg et al. |
| 2003/0191414 A1 | 10/2003 | Reiley et al. |
| 2003/0191489 A1 | 10/2003 | Reiley et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0199979 A1 | 10/2003 | McGuckin, Jr. |
| 2003/0220648 A1 | 11/2003 | Osorio et al. |
| 2003/0220695 A1 | 11/2003 | Sevrain |
| 2003/0229372 A1 | 12/2003 | Reiley et al. |
| 2003/0233096 A1 | 12/2003 | Osorio et al. |
| 2004/0010251 A1 | 1/2004 | Pitaru et al. |
| 2004/0010260 A1 | 1/2004 | Scribner et al. |
| 2004/0010263 A1 | 1/2004 | Boucher et al. |
| 2004/0019354 A1 | 1/2004 | Johnson et al. |
| 2004/0024408 A1 | 2/2004 | Burkus et al. |
| 2004/0024409 A1 | 2/2004 | Sand et al. |
| 2004/0024463 A1 | 2/2004 | Thomas, Jr. et al. |
| 2004/0024465 A1 | 2/2004 | Lambrecht et al. |
| 2004/0034429 A1 | 2/2004 | Lambrecht et al. |
| 2004/0049203 A1 | 3/2004 | Scribner et al. |
| 2004/0059333 A1 | 3/2004 | Carl et al. |
| 2004/0059339 A1 | 3/2004 | Roehm, III et al. |
| 2004/0059418 A1 | 3/2004 | McKay et al. |
| 2004/0064144 A1 | 4/2004 | Johnson et al. |
| 2004/0073308 A1 | 4/2004 | Kuslich et al. |
| 2004/0082953 A1 | 4/2004 | Petit |
| 2004/0087947 A1 | 5/2004 | Lim et al. |
| 2004/0092933 A1 | 5/2004 | Shaolian et al. |
| 2004/0092948 A1 | 5/2004 | Stevens et al. |
| 2004/0092988 A1 | 5/2004 | Shaolian et al. |
| 2004/0097924 A1 | 5/2004 | Lambrecht et al. |
| 2004/0097930 A1 | 5/2004 | Justis et al. |
| 2004/0097932 A1 | 5/2004 | Ray, III et al. |
| 2004/0098131 A1 | 5/2004 | Bryan et al. |
| 2004/0102774 A1 | 5/2004 | Trieu |
| 2004/0106940 A1 | 6/2004 | Shaolian et al. |
| 2004/0111161 A1 | 6/2004 | Trieu |
| 2004/0117019 A1 | 6/2004 | Trieu et al. |
| 2004/0133229 A1 | 7/2004 | Lambrecht et al. |
| 2004/0133280 A1 | 7/2004 | Trieu |
| 2004/0138748 A1 | 7/2004 | Boyer, II et al. |
| 2004/0153064 A1 | 8/2004 | Foley et al. |
| 2004/0153115 A1 | 8/2004 | Reiley et al. |
| 2004/0158206 A1 | 8/2004 | Aboul-Hosn et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0176775 A1 | 9/2004 | Burkus et al. |
| 2004/0186471 A1 | 9/2004 | Trieu |
| 2004/0186528 A1 | 9/2004 | Ries et al. |
| 2004/0186573 A1 | 9/2004 | Ferree |
| 2004/0210231 A1 | 10/2004 | Boucher et al. |
| 2004/0210310 A1 | 10/2004 | Trieu |
| 2004/0215344 A1 | 10/2004 | Hochschuler et al. |
| 2004/0220580 A1 | 11/2004 | Johnson et al. |
| 2004/0220672 A1 | 11/2004 | Shadduck |
| 2004/0225296 A1 | 11/2004 | Reiss et al. |
| 2004/0225361 A1 | 11/2004 | Glenn et al. |
| 2004/0230191 A1 | 11/2004 | Frey et al. |
| 2004/0230309 A1 | 11/2004 | DiMauro et al. |
| 2004/0249377 A1 | 12/2004 | Kaes et al. |
| 2004/0254520 A1 | 12/2004 | Porteous et al. |
| 2004/0254644 A1 | 12/2004 | Taylor |
| 2004/0260300 A1 | 12/2004 | Gorensek et al. |
| 2004/0260397 A1 | 12/2004 | Lambrecht et al. |
| 2004/0267271 A9 | 12/2004 | Scribner et al. |
| 2005/0004578 A1 | 1/2005 | Lambrecht et al. |
| 2005/0010293 A1 | 1/2005 | Zucherman et al. |
| 2005/0010298 A1 | 1/2005 | Zucherman et al. |
| 2005/0015148 A1 | 1/2005 | Jansen et al. |
| 2005/0015152 A1 | 1/2005 | Sweeney |
| 2005/0033295 A1 | 2/2005 | Wisnewski |
| 2005/0033440 A1 | 2/2005 | Lambrecht et al. |
| 2005/0038517 A1 | 2/2005 | Carrison et al. |
| 2005/0043737 A1 | 2/2005 | Reiley et al. |
| 2005/0043796 A1 | 2/2005 | Grant et al. |
| 2005/0055097 A1 | 3/2005 | Grunberg et al. |
| 2005/0060036 A1 | 3/2005 | Schultz et al. |
| 2005/0060038 A1 | 3/2005 | Lambrecht et al. |
| 2005/0065519 A1 | 3/2005 | Michelson |
| 2005/0065609 A1 | 3/2005 | Wardlaw |
| 2005/0069571 A1 | 3/2005 | Slivka et al. |
| 2005/0070908 A1 | 3/2005 | Cragg |
| 2005/0070911 A1 | 3/2005 | Carrison et al. |
| 2005/0070913 A1 | 3/2005 | Milbocker et al. |
| 2005/0071011 A1 | 3/2005 | Ralph et al. |
| 2005/0080488 A1 | 4/2005 | Schultz |
| 2005/0090833 A1 | 4/2005 | DiPoto |
| 2005/0090852 A1 | 4/2005 | Layne et al. |
| 2005/0090899 A1 | 4/2005 | DiPoto |
| 2005/0107880 A1 | 5/2005 | Shimp et al. |

| | | |
|---|---|---|
| 2005/0113918 A1 | 5/2005 | Messerli et al. |
| 2005/0113919 A1 | 5/2005 | Cragg et al. |
| 2005/0113928 A1 | 5/2005 | Cragg et al. |
| 2005/0118228 A1 | 6/2005 | Trieu |
| 2005/0119662 A1 | 6/2005 | Reiley et al. |
| 2005/0119750 A1 | 6/2005 | Studer |
| 2005/0119751 A1 | 6/2005 | Lawson |
| 2005/0119752 A1 | 6/2005 | Williams et al. |
| 2005/0119754 A1 | 6/2005 | Trieu et al. |
| 2005/0124989 A1 | 6/2005 | Suddaby |
| 2005/0124992 A1 | 6/2005 | Ferree |
| 2005/0124999 A1 | 6/2005 | Teitelbaum et al. |
| 2005/0125066 A1 | 6/2005 | McAfee |
| 2005/0131267 A1 | 6/2005 | Talmadge |
| 2005/0131268 A1 | 6/2005 | Talmadge |
| 2005/0131269 A1 | 6/2005 | Talmadge |
| 2005/0131536 A1 | 6/2005 | Eisermann et al. |
| 2005/0131540 A1 | 6/2005 | Trieu |
| 2005/0131541 A1 | 6/2005 | Trieu |
| 2005/0137602 A1 | 6/2005 | Assell et al. |
| 2005/0142211 A1 | 6/2005 | Wenz |
| 2005/0143763 A1 | 6/2005 | Ortiz et al. |
| 2005/0143827 A1 | 6/2005 | Globerman et al. |
| 2005/0149022 A1 | 7/2005 | Shaolian et al. |
| 2005/0149191 A1 | 7/2005 | Cragg et al. |
| 2005/0149194 A1 | 7/2005 | Ahlgren |
| 2005/0149197 A1 | 7/2005 | Cauthen |
| 2005/0154396 A1 | 7/2005 | Foley et al. |
| 2005/0154463 A1 | 7/2005 | Trieu |
| 2005/0165406 A1 | 7/2005 | Assell et al. |
| 2005/0171539 A1 | 8/2005 | Braun et al. |
| 2005/0171552 A1 | 8/2005 | Johnson et al. |
| 2005/0182412 A1 | 8/2005 | Johnson et al. |
| 2005/0182413 A1 | 8/2005 | Johnson et al. |
| 2005/0182414 A1 | 8/2005 | Manzi et al. |
| 2005/0187556 A1 | 8/2005 | Stack et al. |
| 2005/0187558 A1 | 8/2005 | Johnson et al. |
| 2005/0187559 A1 | 8/2005 | Raymond et al. |
| 2005/0187564 A1 | 8/2005 | Jayaraman |
| 2005/0197707 A1 | 9/2005 | Trieu et al. |
| 2005/0216087 A1 | 9/2005 | Zucherman et al. |
| 2005/0222684 A1 | 10/2005 | Ferree |
| 2005/0228383 A1 | 10/2005 | Zucherman et al. |
| 2005/0228391 A1 | 10/2005 | Levy et al. |
| 2005/0228397 A1 | 10/2005 | Malandain et al. |
| 2005/0234425 A1 | 10/2005 | Miller et al. |
| 2005/0234451 A1 | 10/2005 | Markworth |
| 2005/0234452 A1 | 10/2005 | Malandain |
| 2005/0234456 A1 | 10/2005 | Malandain |
| 2005/0240182 A1 | 10/2005 | Zucherman et al. |
| 2005/0240189 A1 | 10/2005 | Rousseau et al. |
| 2005/0240193 A1 | 10/2005 | Layne et al. |
| 2005/0240269 A1 | 10/2005 | Lambrecht et al. |
| 2005/0251149 A1 | 11/2005 | Wenz |
| 2005/0251260 A1 | 11/2005 | Gerber et al. |
| 2005/0261684 A1 | 11/2005 | Shaolian et al. |
| 2005/0261695 A1 | 11/2005 | Cragg et al. |
| 2005/0261781 A1 | 11/2005 | Sennett et al. |
| 2005/0273166 A1 | 12/2005 | Sweeney |
| 2005/0273173 A1 | 12/2005 | Gordon |
| 2005/0278027 A1 | 12/2005 | Hyde, Jr. |
| 2005/0278029 A1 | 12/2005 | Trieu |
| 2005/0283244 A1 | 12/2005 | Gordon et al. |
| 2005/0287071 A1 | 12/2005 | Wenz |
| 2006/0004456 A1 | 1/2006 | McKay |
| 2006/0009779 A1 | 1/2006 | Collins et al. |
| 2006/0030850 A1 | 2/2006 | Keegan et al. |
| 2006/0030943 A1 | 2/2006 | Peterman |
| 2006/0036241 A1 | 2/2006 | Siegal |
| 2006/0036259 A1 | 2/2006 | Carl et al. |
| 2006/0036261 A1 | 2/2006 | McDonnell |
| 2006/0036273 A1 | 2/2006 | Siegal |
| 2006/0058807 A1 | 3/2006 | Landry et al. |
| 2006/0058880 A1 | 3/2006 | Wysocki et al. |
| 2006/0064171 A1 | 3/2006 | Trieu |
| 2006/0069439 A1 | 3/2006 | Zucherman et al. |
| 2006/0069440 A1 | 3/2006 | Zucherman et al. |
| 2006/0085002 A1 | 4/2006 | Trieu et al. |
| 2006/0085009 A1 | 4/2006 | Truckai et al. |
| 2006/0089642 A1 | 4/2006 | Diaz et al. |
| 2006/0089646 A1 | 4/2006 | Bonutti |
| 2006/0089654 A1 | 4/2006 | Lins et al. |
| 2006/0089718 A1 | 4/2006 | Zucherman et al. |
| 2006/0089719 A1 | 4/2006 | Trieu |
| 2006/0095045 A1 | 5/2006 | Trieu |
| 2006/0095046 A1 | 5/2006 | Trieu et al. |
| 2006/0095134 A1 | 5/2006 | Trieu et al. |
| 2006/0095138 A1 | 5/2006 | Truckai et al. |
| 2006/0100706 A1 | 5/2006 | Shadduck et al. |
| 2006/0106397 A1 | 5/2006 | Lins |
| 2006/0106459 A1 | 5/2006 | Truckai et al. |
| 2006/0122704 A1 | 6/2006 | Vresilovic et al. |
| 2006/0129244 A1 | 6/2006 | Ensign |
| 2006/0136064 A1 | 6/2006 | Sherman |
| 2006/0142858 A1 | 6/2006 | Colleran et al. |
| 2006/0142864 A1 | 6/2006 | Cauthen |
| 2006/0149136 A1 | 7/2006 | Seto et al. |
| 2006/0149237 A1 | 7/2006 | Markworth et al. |
| 2006/0149252 A1 | 7/2006 | Markworth et al. |
| 2006/0149379 A1 | 7/2006 | Kuslich et al. |
| 2006/0149380 A1 | 7/2006 | Lotz et al. |
| 2006/0155379 A1 | 7/2006 | Heneveld et al. |
| 2006/0161162 A1 | 7/2006 | Lambrecht et al. |
| 2006/0161166 A1 | 7/2006 | Johnson et al. |
| 2006/0167553 A1 | 7/2006 | Cauthen, III et al. |
| 2006/0173545 A1 | 8/2006 | Cauthen, III et al. |
| 2006/0178746 A1 | 8/2006 | Bartish et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0189999 A1 | 8/2006 | Zwirkoski |
| 2006/0190083 A1 | 8/2006 | Arnin et al. |
| 2006/0190085 A1 | 8/2006 | Cauthen |
| 2006/0195102 A1 | 8/2006 | Malandain |
| 2006/0195191 A1 | 8/2006 | Sweeney et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0235423 A1 | 10/2006 | Cantu |
| 2006/0235521 A1 | 10/2006 | Zucherman et al. |
| 2006/0241663 A1 | 10/2006 | Rice et al. |
| 2006/0241770 A1 | 10/2006 | Rhoda et al. |
| 2006/0247770 A1 | 11/2006 | Peterman |
| 2006/0247771 A1 | 11/2006 | Peterman et al. |
| 2006/0247781 A1 | 11/2006 | Francis |
| 2006/0264896 A1 | 11/2006 | Palmer |
| 2006/0264939 A1 | 11/2006 | Zucherman et al. |
| 2006/0264945 A1 | 11/2006 | Edidin et al. |
| 2006/0265067 A1 | 11/2006 | Zucherman et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276897 A1 | 12/2006 | Winslow |
| 2006/0282167 A1 | 12/2006 | Lambrecht et al. |
| 2006/0293662 A1 | 12/2006 | Boyer, II et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010717 A1 | 1/2007 | Cragg |
| 2007/0010824 A1 | 1/2007 | Malandain et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010889 A1 | 1/2007 | Francis |
| 2007/0032703 A1 | 2/2007 | Sankaran et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0048382 A1 | 3/2007 | Meyer et al. |
| 2007/0049849 A1 | 3/2007 | Schwardt et al. |

| | | |
|---|---|---|
| 2007/0049934 A1 | 3/2007 | Edidin et al. |
| 2007/0049935 A1 | 3/2007 | Edidin et al. |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055237 A1 | 3/2007 | Edidin et al. |
| 2007/0055246 A1 | 3/2007 | Zucherman et al. |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055271 A1 | 3/2007 | Schaller |
| 2007/0055272 A1 | 3/2007 | Schaller |
| 2007/0055273 A1 | 3/2007 | Schaller |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0068329 A1 | 3/2007 | Phan et al. |
| 2007/0073292 A1 | 3/2007 | Kohm et al. |
| 2007/0078436 A1 | 4/2007 | Leung et al. |
| 2007/0078463 A1 | 4/2007 | Malandain |
| 2007/0093689 A1 | 4/2007 | Steinberg |
| 2007/0093899 A1 | 4/2007 | Dutoit et al. |
| 2007/0093906 A1 | 4/2007 | Hudgins et al. |
| 2007/0123986 A1 | 5/2007 | Schaller |
| 2007/0135922 A1 | 6/2007 | Trieu |
| 2007/0149978 A1 | 6/2007 | Shezifi et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0162127 A1 | 7/2007 | Peterman et al. |
| 2007/0167945 A1 | 7/2007 | Lange et al. |
| 2007/0168038 A1 | 7/2007 | Trieu |
| 2007/0179612 A1 | 8/2007 | Johnson et al. |
| 2007/0179615 A1 | 8/2007 | Heinz et al. |
| 2007/0179616 A1 | 8/2007 | Braddock, Jr. et al. |
| 2007/0179618 A1 | 8/2007 | Trieu et al. |
| 2007/0185578 A1 | 8/2007 | O'Neil et al. |
| 2007/0191953 A1 | 8/2007 | Trieu |
| 2007/0197935 A1 | 8/2007 | Reiley et al. |
| 2007/0198023 A1 | 8/2007 | Sand et al. |
| 2007/0198025 A1 | 8/2007 | Trieu et al. |
| 2007/0208426 A1 | 9/2007 | Trieu |
| 2007/0213717 A1 | 9/2007 | Trieu et al. |
| 2007/0219634 A1 | 9/2007 | Greenhalgh et al. |
| 2007/0233074 A1 | 10/2007 | Anderson et al. |
| 2007/0260255 A1 | 11/2007 | Haddock et al. |
| 2007/0270957 A1 | 11/2007 | Heinz |
| 2007/0282443 A1 | 12/2007 | Globerman et al. |
| 2008/0021557 A1 | 1/2008 | Trieu |
| 2008/0027437 A1 | 1/2008 | Johnson et al. |
| 2008/0027453 A1 | 1/2008 | Johnson et al. |
| 2008/0027454 A1 | 1/2008 | Johnson et al. |
| 2008/0221687 A1* | 9/2008 | Viker ........................ 623/17.16 |
| 2008/0229597 A1 | 9/2008 | Malandain |
| 2008/0281346 A1 | 11/2008 | Greenhalgh et al. |
| 2008/0281364 A1 | 11/2008 | Chirico et al. |
| 2009/0048678 A1 | 2/2009 | Saal et al. |

FOREIGN PATENT DOCUMENTS

| | | |
|---|---|---|
| EP | 0529275 A2 | 3/1993 |
| EP | 0 621 020 A1 | 10/1994 |
| EP | 1 157 676 A1 | 4/2001 |
| WO | WO 01/10316 A1 | 2/2001 |
| WO | WO 02/17824 A2 | 3/2002 |
| WO | WO 02/30338 A1 | 4/2002 |
| WO | WO 02/43628 A1 | 6/2002 |
| WO | WO 02/47563 A1 | 6/2002 |
| WO | WO 02/071921 A2 | 9/2002 |
| WO | WO 03/007854 A1 | 1/2003 |
| WO | WO 03/020169 A2 | 3/2003 |
| WO | WO 03/022165 A1 | 3/2003 |
| WO | WO 03/028587 A2 | 4/2003 |
| WO | WO 03/059180 A2 | 7/2003 |
| WO | WO2004/034924 A2 | 4/2004 |
| WO | WO 2004/082526 A2 | 9/2004 |
| WO | WO 2004/108022 A1 | 12/2004 |
| WO | WO 2005/032433 A2 | 4/2005 |
| WO | WO 2005/051246 A2 | 6/2005 |
| WO | WO 2005/081877 A2 | 9/2005 |
| WO | WO 2006/047645 A2 | 5/2006 |
| WO | WO 2006/060420 A1 | 6/2006 |
| WO | WO 2006/066228 A2 | 6/2006 |
| WO | WO 2006/072941 A2 | 7/2006 |
| WO | WO 2007/022194 A2 | 2/2007 |
| WO | WO2007/067726 A2 | 6/2007 |

* cited by examiner

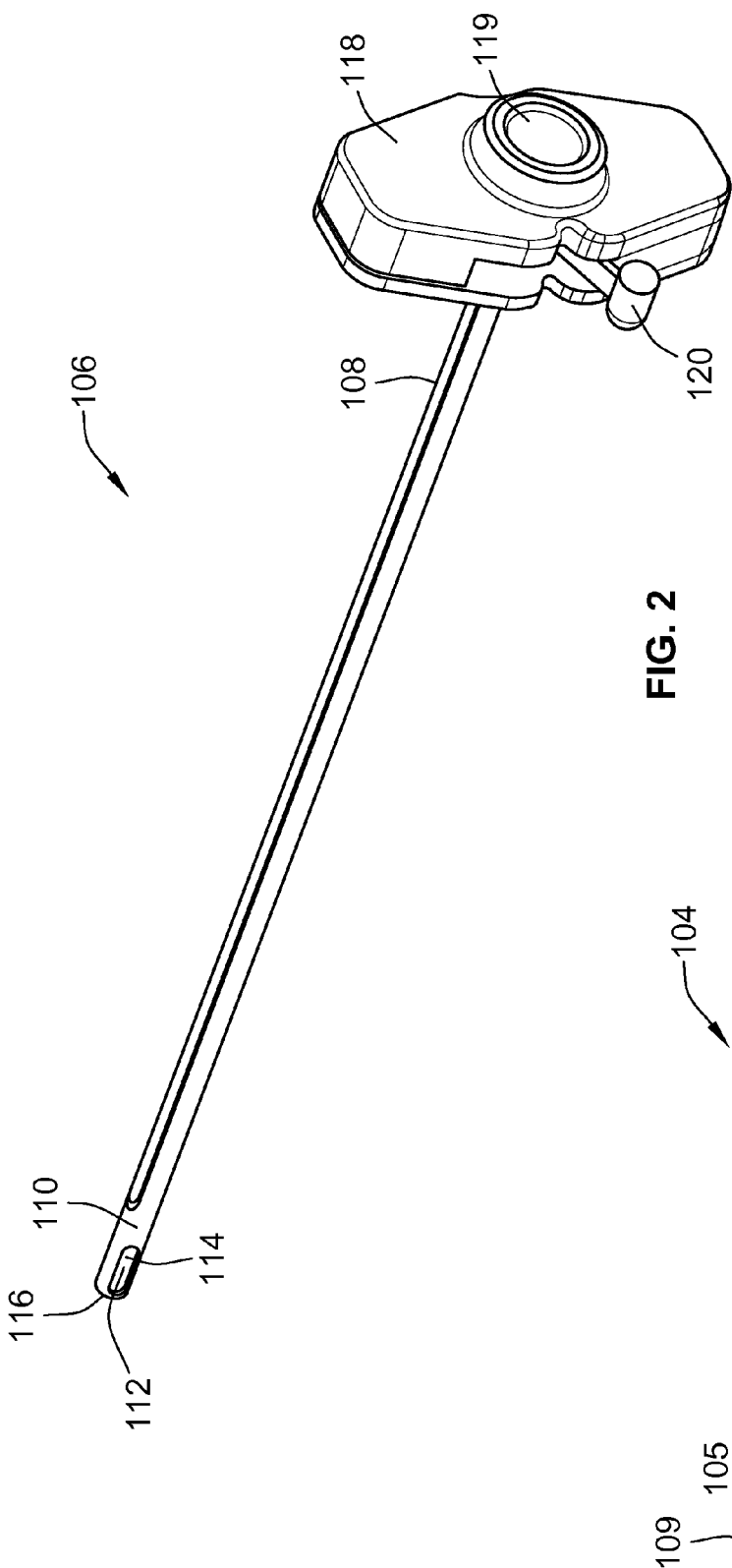
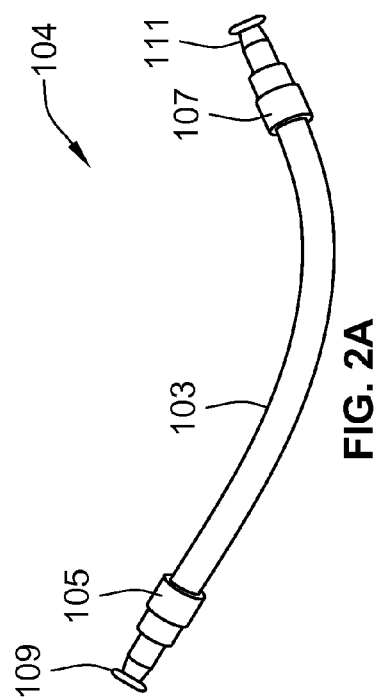
FIG. 2
FIG. 2A

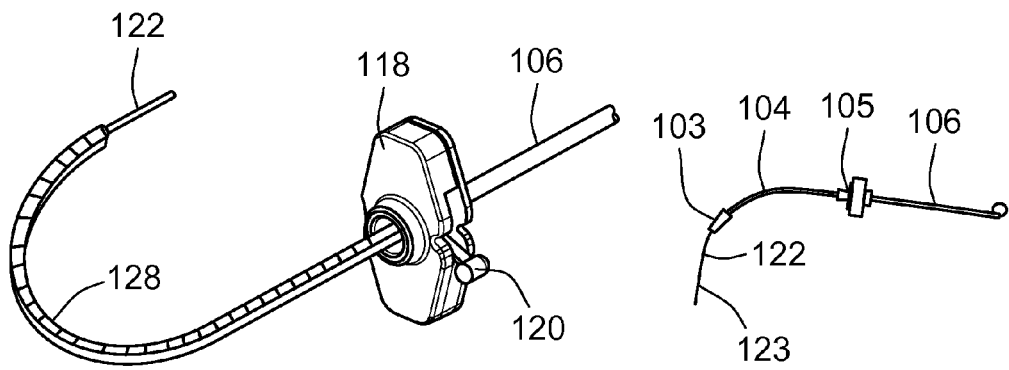
FIG. 12      FIG. 13
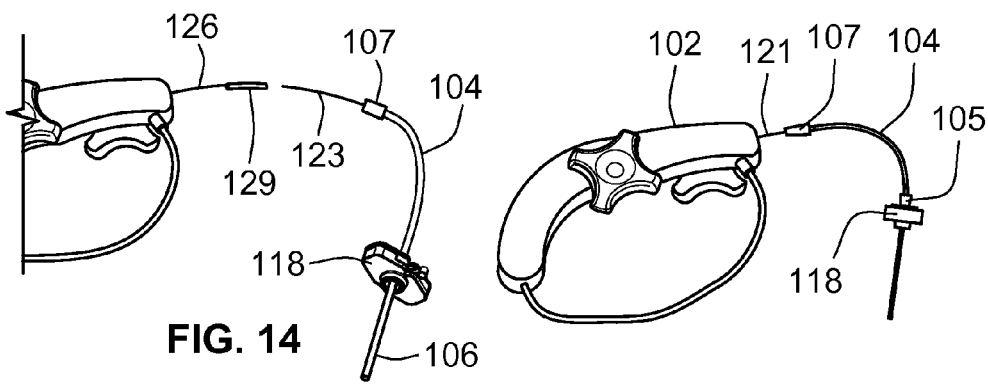
FIG. 14      FIG. 15
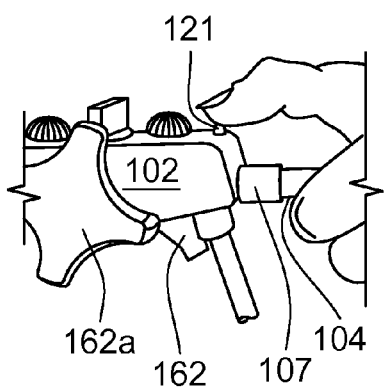
FIG. 16

DELIVERY APPARATUS FOR USE WITH IMPLANTABLE MEDICAL DEVICES

The present application claims the benefit of U.S. Provisional Patent Application Ser. No. 61/160,882 which was filed Mar. 17, 2009 and is hereby incorporated herein by reference.

The present application generally relates to apparatus and methods that are utilized to deploy therapeutic medical devices into a patient. In particular, the present application relates to delivery apparatus and methods that can be utilized in minimally invasive surgical procedures to implant prosthetic devices into spinal tissue.

BACKGROUND

A variety of physical conditions can be treated by implanting a therapeutic medical device, such as a prosthetic, into a patient. Several implantable medical devices require the use of a guide wire for deployment into the patient. Typically, the guide wire is inserted into the patient to guide the medical device to a desired treatment site, and oftentimes, ensures that the implantable device is in the desire orientation and/or configuration. The therapeutic medical device is navigated over or along the guide wire to implant the medical device at the desired location within the patient.

One location of the body where prosthetic implantation is useful as a corrective treatment is in the spinal column. Developmental irregularities, trauma, tumors, stress and degenerative wear can cause defects in the spinal column for which surgical intervention is necessary. Some of the more common defects of the spinal column include vertebral compression fractures, degeneration or disruption of an intervertebral disc and intervertebral disc herniation. These and other pathologies of the spine are often treated with implants or prosthetics that can restore vertebral column height, immobilize or fuse adjacent vertebral bones, or function to provide flexibility and restore natural movement of the spinal column.

In the past, spinal corrective surgeries often required open invasive procedures in order to access and implant devices into the spine. Recently, however, there have been several advances in minimally invasive surgical techniques, which provide many benefits over the open invasive procedures. Along with such advancements has come the development of several minimally invasive implantable spinal devices. Examples of such device can be found in co-owned U.S. patent application Ser. No. 12/034,853, filed Feb. 21, 2008 and Ser. No. 11/464,782, filed Aug. 15, 2006, both of which are hereby incorporated by reference.

SUMMARY

The delivery apparatus and methods of the present disclosure can be utilized to delivery implantable medical devices into a patient, and are particularly useful for delivery of spinal implants or prosthetics. The delivery apparatus can be used in minimally invasive procedures to both deploy a guide member, such as a guide wire, and deliver an implantable medical device along the guide wire and into a treatment site. One of the advantages provided by the delivery apparatus is that one device can be used to deploy both the guide wire and the implantable device, which reduces the number of tools required for a procedure and also reduces the need for multiple access sites or repeated insertion and withdrawal through a single access site into and out of the target or treatment site.

According to one aspect of the present disclosure, the delivery apparatus includes a housing and a cannula having a proximal end operatively connected to the housing. The cannula includes a distal end portion that has a distal end opening and is adapted for insertion into a treatment site. In one embodiment, the cannula is sized and shaped to be inserted through a minimally invasive access site and into spinal tissue, such as a vertebral body or an intervertebral disc. The delivery apparatus also includes a guide member that has a distal end portion that is disposable within the cannula and has a proximal end portion that is at least partially disposed within the housing. The guide member is advanceable through the cannula, out the distal end opening of the cannula and into the treatment site, which may be, for example, the interior of a vertebral body. The guide member is adapted for advancement of an implant therealong so that the guide member guides the implant through the cannula, out of the distal end opening of the cannula and into the treatment site. Further, the delivery apparatus also includes a pushing element that has a distal end portion that is disposable within the cannula and a proximal end portion at least partially disposed within the housing. The pushing element is advanceable relative to the guide member and pushes the implant along the guide member. The housing includes a drive system that advance the guide member and the pushing element.

The drive mechanism may employ any suitable principle, and as illustrated can be a friction drive mechanism in which the guide wire and/or pusher member pass between a drive element and a facing or compression member. The compression member applies load (e.g., pinches the guide wire and pusher member between the drive element and compression member) to create frictional engagement that facilitates the ability of the drive member to drive the pusher member and the guide wire in either the distal or proximal directions. Alternatively, the drive mechanism can be a gear drive mechanism, such as a rack and pinion-type assembly, in which the guide wire and pusher member include rack teeth that mesh with pinion teeth of a drive shaft. Yet in another alternative embodiment, the drive mechanism may be a carriage-style mechanism in which the guide member and pusher member are wound around a carriage or spool. Other suitable drive systems may also be employed.

According to another aspect, the delivery apparatus may include a handle and/or housing and a cannula operatively connected thereto. The cannula includes a proximal end portion, a distal end portion and an interior lumen extending through the cannula. The cannula is adapted for insertion into a patient to place the distal end portion at or near a treatment site, such as a damaged vertebral body or intervertebral disc. The delivery apparatus may also include a guide wire located at least partially within the housing or handle. The guide wire is advanceable from the housing through the lumen of the cannula and into the treatment site. The guide wire includes a distal end portion that has a first configuration when disposed within the cannula and a second configuration upon being advanced out of the cannula and into the treatment site. The guide wire is adapted to have an implant advanced along the guide member so that the guide wire guides in the implant through the lumen of the cannula, out of the distal end of the cannula and into a pre-selected shape within the treatment site. A pushing element is operatively associated with the guide wire for advancing the implant along the guide wire. The housing also includes a drive system for advancing the guide wire and pushing element.

In yet another aspect, a method of the present disclosure includes inserting a cannula into a patient and placing the distal end portion of the cannula at or near a treatment site. A drive system is activated to advance a guide wire through the cannula and out of the distal end portion of the cannula into the treatment site. The drive system then is activated to advance, such as by a pusher member, an implantable medical device along the guide wire, through the cannula and into the treatment site, thereby implanting the implantable medical device. After the implantable medical device is in the desired position, the drive system is activated to retract the guide wire from the treatment site. Once the guide wire is retracted, the drive mechanism may be activated to retract the pusher member, if necessary, back through the cannula.

These and other aspects of the present invention are set forth in the following detailed description. In that respect, it should be noted that the present invention includes a number of different aspects which may have utility alone and/or in combination with other aspects. Accordingly, the above summary is not exhaustive identification of each such aspect that is now or may hereafter be claimed, but represents an overview of the present invention to assist in understanding the more detailed description that follows. The scope of the invention is as set forth in the claims now or hereafter filed.

BRIEF DESCRIPTION OF THE FIGURES

In the course of this description, reference will be made to the accompanying drawings, wherein:

FIG. 2 is a perspective view of one embodiment of a delivery cannula of the delivery apparatus shown in FIG. 1;

FIG. 2A is a perspective view of one embodiment of a flexible or bridge member of the delivery apparatus shown in FIG. 1;

FIGS. 12-16 illustrate a loading and assembly sequence of the delivery apparatus shown in FIG. 1.

DETAILED DESCRIPTION

Several implantable medical devices, such as implantable prosthetic devices, require the use of a guide wire to implant the device at a desired location within a patient. As used herein, the terms "implantable device," "implant" and "implantable medical device" refer to devices that are intended to be permanently implanted or temporarily implanted, even for a very short period of time, within a patient. The delivery apparatus and methods described herein facilitate deployment of the guide wire into the treatment site and the navigation of an implantable medical device over or along the guide wire for deployment of the device into the treatment site. Although the apparatus and methods disclosed herein are particularly well suited for delivering prosthetic devices into spinal tissue, such as a vertebral body or an intervertebral disc, the apparatus and methods can also be used to deliver implantable devices into other areas of the body as well.

The apparatus and methods described herein can be particularly useful with the medical devices and procedures disclosed in the following co-owned patent applications: U.S. application Ser. Nos. 12/034,853 and 12/035,298, both of which were filed Feb. 21, 2008, and Ser. No. 11/464,782, which was filed Aug. 15, 2006. All of the foregoing co-owned applications are hereby incorporated herein by reference.

Figure 1:
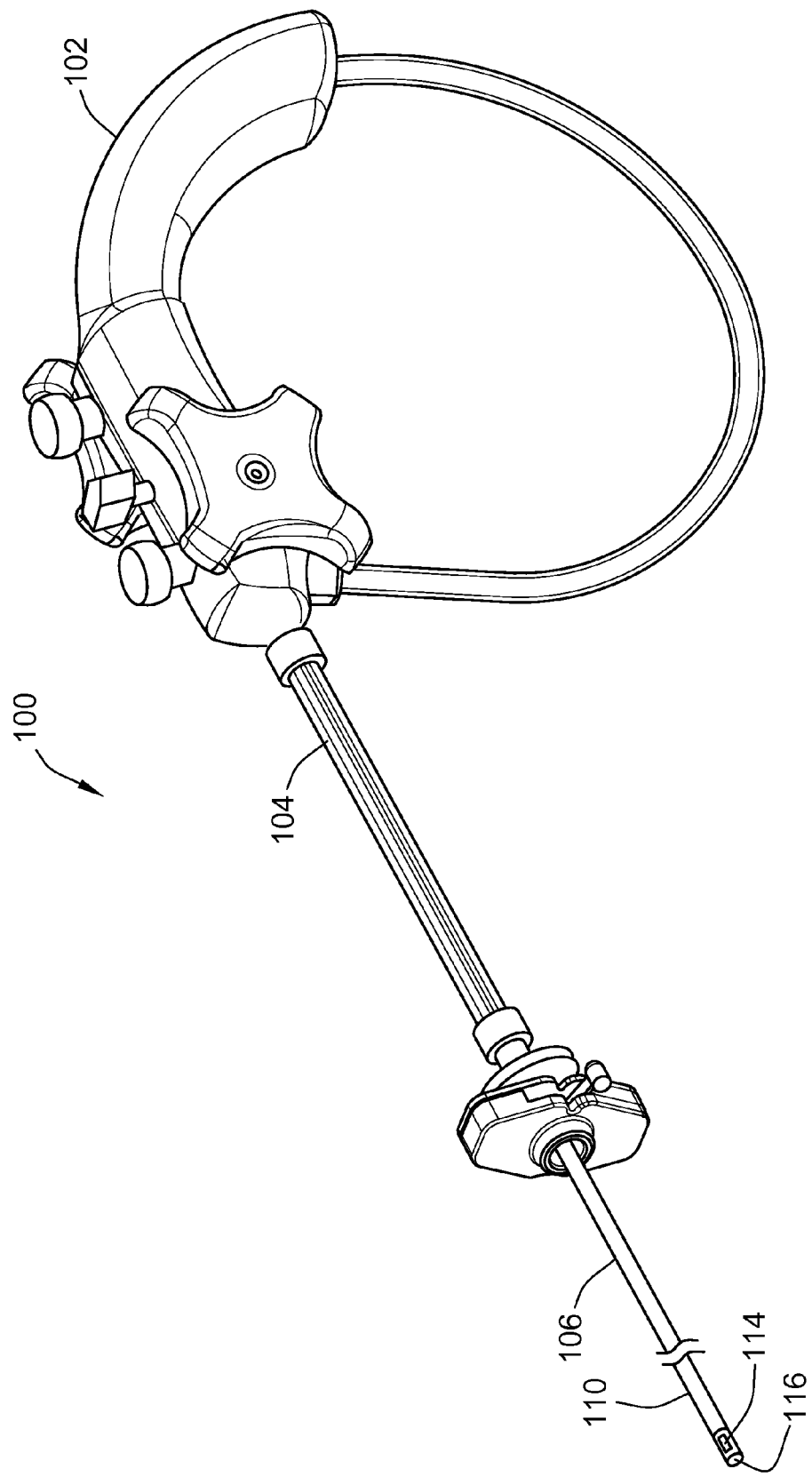
FIG. 1 is a perspective view of one embodiment of a delivery apparatus constructed in accordance with the present disclosure.

FIG. 1 illustrates one embodiment of a delivery apparatus 100 that can be used to implant a medical device into a patient. The delivery apparatus 100 includes a housing 102, a flexible element, extension or bridge member 104 and a delivery cannula 106. When in use, the distal end portion 110 of delivery cannula 106 is inserted into a treatment site, preferably through a minimally invasive access site. A drive mechanism, which will be discussed in more detail below, is then utilized to advance a guide member, such as a guide wire, from the housing through the flexible bridge 104, through the cannula and out of an opening 114 in the distal end portion 110 of the delivery cannula 106 into the treatment site. The guide wire can be an elongated member, such as an elongated thread or ribbon. After the guide wire is in the desired position, the drive mechanism is then used to advance a pushing element, such as a pusher member, from the housing and along the guide wire. The pusher member pushes or otherwise causes an implantable medical device, such as a prosthetic, to be advanced or otherwise translated along the guide wire through the delivery cannula and into the treatment site. After the implant is in the desired position, the pusher member can be retracted and the guide wire can be retracted or severed. The guide wire, pusher and the method of deploying a prosthetic implant will be discussed in more detail below.

Referring to FIG. 2, the delivery cannula 106 may have an elongated generally cylindrical shape and includes a proximal end portion 108 and distal end portion 110. Preferably, the length of the delivery cannula 106 is sufficient to place the distal end portion 110 of the cannula 106 at a desired location within a patient. Accordingly, the length of the delivery cannula 106 can vary depending on the particular procedure, location of treatment and the condition to be treated. In one embodiment the length of the delivery cannula 106 is between about 4 inches and about 8 inches.

The delivery cannula 106 includes an interior lumen 112 sized for receiving a guide member and an implantable medical device therethrough. The cross-sectional width of the interior lumen 112 and the outer cross-sectional width of the delivery cannula 106, which can be diameters when the delivery cannula has a generally circular cross-sectional shape, can vary greatly depending on the type of procedure and the size of the medical device being implanted. When used in minimally invasive surgical procedures, the cannula 106 is preferably sized to be inserted through a relatively small access hole or site. Thus, the cross-sectional width of the interior lumen 112 and the outer cross-sectional width of the delivery cannula 106 are preferably no larger than what is require to allow passage of a guide wire and an implantable medical device through the delivery cannula 106. In one embodiment, the outer cross-sectional width of the delivery cannula is between about 0.15 inches and about 0.35 inches, and the cross-sectional width of the interior lumen 12 is between about 0.12 inches and 0.34 inches.

The distal end portion 110 of delivery cannula 106 includes opening 114 that communicates with the interior lumen 112. In the illustrated embodiment, the distal tip 116 of delivery cannula 106 is closed and the opening 114 is located in the side of the delivery cannula 106. In an alternative embodiment, the opening 114 can be located in the distal tip 116. The opening 114 at the distal end portion 110 of delivery cannula 106 is sized to allow the guide wire and implant to exit the delivery cannula through the opening 114 and into treatment site. At the proximal end portion 108 of delivery cannula 106 is located as an attachment mechanism, such as an attachment member 118. The attachment member 118 can include a locking feature that can releasably attach the cannula 106 to the flexible extension or bridge member 104 or to the housing when a flexible bridge member is not utilized.

The attachment member 118 of the delivery cannula 106 is preferably mounted on the proximal end portion 108 of the delivery cannula 106. The attachment member 118 can be integrally constructed with cannula 106 or may be a separate piece that is attached to the cannula 106. In the illustrated embodiment, the attachment member 118 includes an opening 119, a locking mechanism, for example a lock clip (not shown) or a lever 120. Opening 119 communicates with interior lumen 112 of the cannula and is sized to receive the distal end portion of the flexible bridge 104. The lever 120 and lock clip interact to move the lock clip from an unlocked position, to a locked position. As explained in more detail below, in the locked position, the lock clip engages the distal end portion of the flexible bridge 104 such that it cannot be separated from the delivery cannula 106.

The delivery apparatus 100 may also include a visual insertion marker or aid that may assist the surgeon during insertion of the delivery cannula 106 into a treatment site. In particular, the visual marker may aid the surgeon in inserting the delivery cannula at the desired angle of trajectory and in the correct orientation.

Figure 2B:
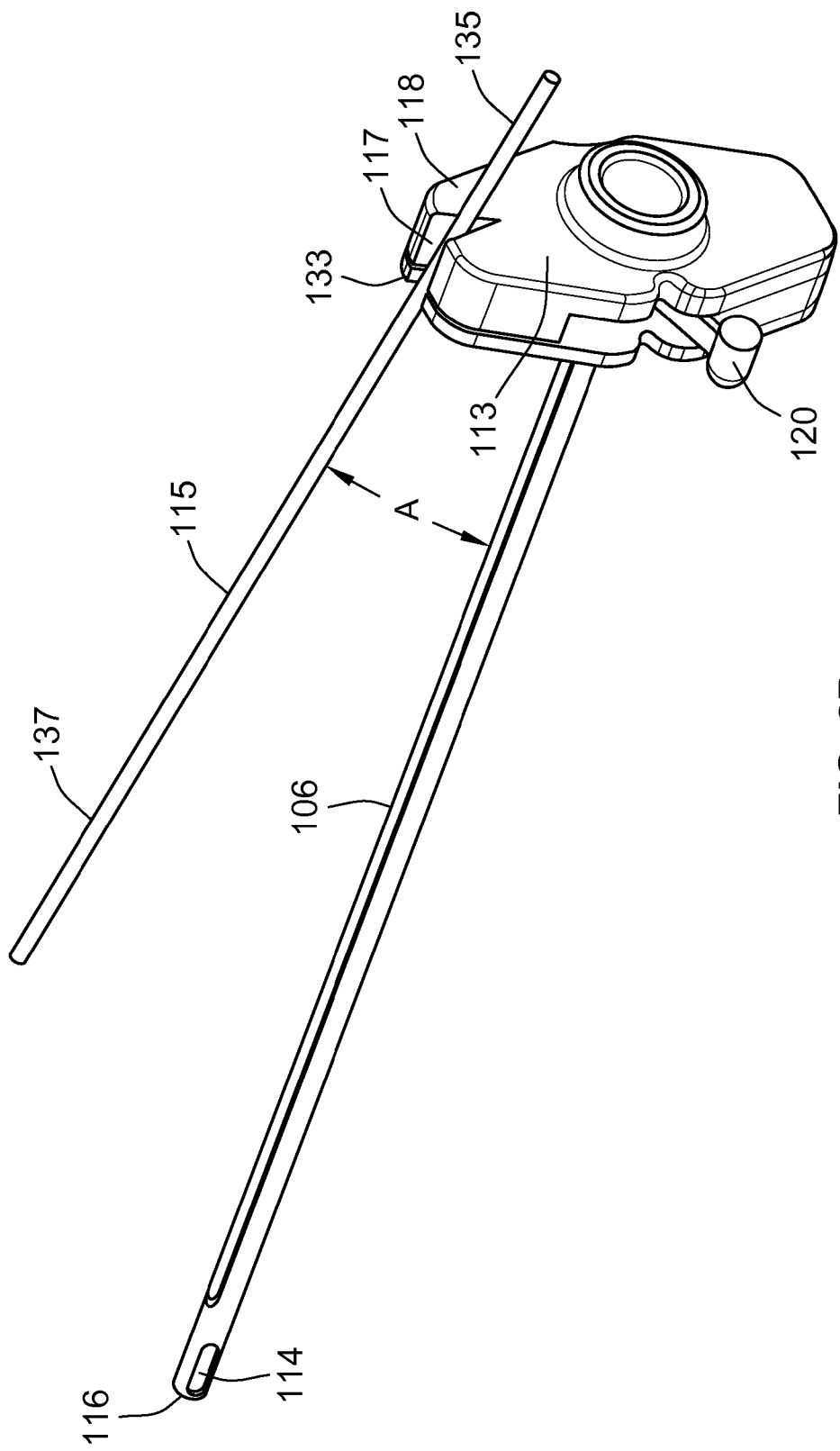
FIG. 2B is a perspective view of another embodiment of a delivery cannula including a visual marker.

As shown in FIG. 2B, the visual marker may include an elongated member 115 that is operatively associated with or attached to the delivery cannula 106. The elongated member 115 is preferably a rod, bar or wire and is constructed from a material that is visible under fluoroscopy or other imaging system. For example, the elongated member 115 may be constructed from a metal or an impregnated polymer.

In the illustrated embodiment, the elongate member is attached, preferably temporarily, to the attachment member 118. As shown, the attachment member 118 may include a slot or an aperture 117 that extends through the attachment member 118 from the front surface 131 through the rear surface 133. The slot 117 is sized to accommodate or hold the elongated member 115. The proximal end or section 135 of the elongated member 115 is place into and held in the slot 117, preferably by friction, snap fit or some other attachment feature. In one embodiment, the slot 117 may have a taper in which the elongated member 115 may be wedged or otherwise frictionally attached to the attachment member 118. The distal end or section 137 of the elongated member 115 extends from the attachment member in a distal direction. The elongated member 115 extends at an angle "A" relative to the delivery cannula 106. Preferably, angle "A" is less than about 90 degrees, and more preferably, between about 30 degrees and about 90 degrees. The angle may be less than about 30 degrees depending on the particular application. In one embodiment, the angle is between about 65 degrees and about 75 degrees.

Under fluoroscopic imaging, the surgeon can visualize the elongated member 115, the delivery cannula 106, and the bone structure of the vertebral body. The elongated member 115 can be identified clearly in the fluoroscopic imaging and provides the surgeon with an additional visual marker that may assist the surgeon in inserting the delivery cannula 106 is the desired orientation and trajectory. For example, the surgeon can utilize the imaginary plane extending between the cannula 106 and elongated member 115 to orientate the cannula relative to the bone structure during insertion of the cannula into the bone.

Because the delivery cannula 106 is exposed to bodily fluids, the delivery cannula 106 may be a disposable/"single-use" article or an article that may be resterilized for multiple use. The cannula 106 may be constructed from materials such as stainless steel, rigid plastic or the like. When the cannula is a multi-use article, it is preferably constructed from materials that can withstand common sterilization techniques.

In the embodiment illustrated in FIG. 1, the delivery cannula 106 is operatively connected to the housing 102 by the flexible bridge or umbilicus 104. Flexible bridge 104 may bend or curve to allow the operator to move the cannula 106 and housing 102 relative to one another. The ability to bend the flexible bridge 104 enhances the operator's ability to manipulate or articulate the delivery apparatus 100 into suitable or desirable positions during the procedure. In one embodiment, the flexible bridge 104 allows the housing 102 to be positioned at a range of angles of from about 0 degrees up to about 90 degrees or even more from the axis of deployment cannula 106. The ability to articulate the housing 102 relative to the cannula 106 may be desirable for several reasons. For example, such articulation may provide space for other surgical devices, such as intraoperative imaging, that otherwise may be difficult to employ without moving the handle to a more convenient location. Further, such articulation allows the operator to alter the location of housing 102 via rotation or translation so as to permit the operator to move the housing as needed to perform the procedure or view the surgical field. Also, the flexible bridge 104 may provide for a degree of mechanical de-coupling or mechanical isolation of the housing 102 and the cannula 106, i.e., the cannula does not necessary move every time the housing is moved. Thus, accidental movement or vibration of the housing 102 is not necessarily translated to the cannula 106. This mechanical decoupling assists in reducing the risk of injury to the patient in such cases as when the housing 102 is accidentally contacted or moved. Another additional benefit of the flexible bridge 104 is that when the bridge is made of a transparent material, such as a transparent polymer, the operator will be able to view the guide wire, pushing element and implant to visually monitor the progress of their deployment.

Referring to FIG. 2A, the flexible bridge 104 includes an elongated hollow tube 103 having distal end portion 105 and proximal end portion 107. Although the flexible bridge 104 is depicted as cylindrical in shape, other shapes may be used as desired. The flexible bridge 104 is preferably sized to slidably receive the guide wire, medical implant, and pusher member and allow easy movement of these element therethrough. The length of the flexible bridge 104 can vary and is of such suitable length as may be required for a particular procedure. In one embodiment, the flexible bridge member 104 has a length of between about 3 inches and about 8 inches. The flexible bridge 104 can be constructed from any suitable material and typically is constructed from flexible materials such as a thermoplastic polymers or more specifically polyvinyl chloride or like material.

The flexible bridge 104 may be an entirely separate piece or alternatively, may be integrally connected to the delivery cannula 106 or the housing 102. In the illustrated embodiment, the flexible bridge 104 is removably attachable to the delivery cannula 106 and the housing 102. Each end portion 105 and 107 of the flexible bridge 104 includes a groove 109 and 111, respectively. To attach the flexible bridge 104 to the delivery cannula 106 distal end portion 105 of the flexible member 104 is inserted into opening 119 of attachment member 118 located at the proximal end portion 108 of delivery cannula 106. The lock lever 120 is then moved into the locked position so that the lock clip engages groove 109. To attach the flexible bridge 104 to the housing, the proximal end portion 107 of the flexible member 104 is inserted into opening 113 (FIG. 8) of housing 102. A lock clip 121 engages groove 111 to secure the flexible bridge 104 to the housing 102. Lock clip 121 and housing 102 are shown in more detail in FIG. 7.

Figure 6:
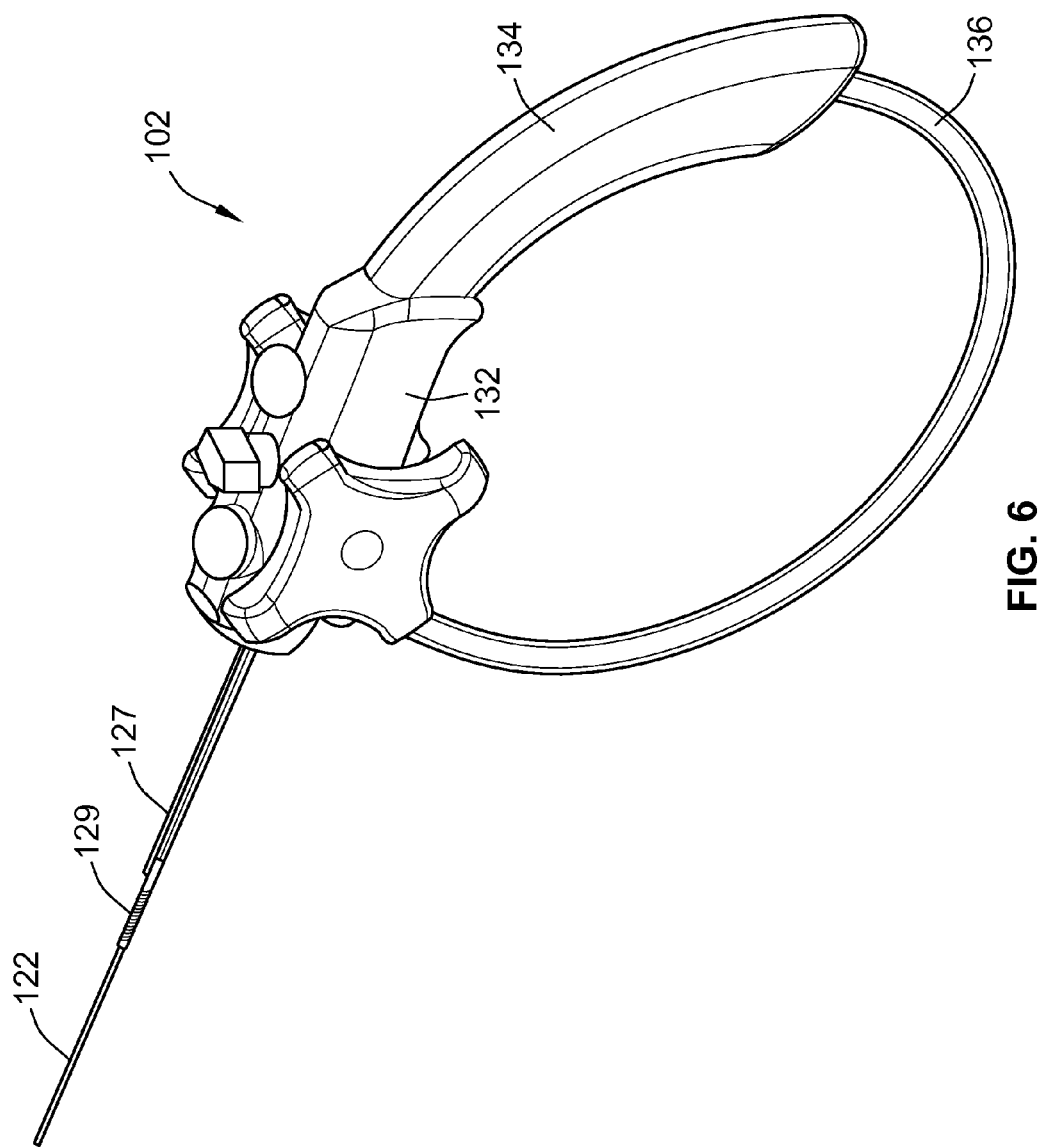
FIG. 6 is a perspective view of one embodiment of the housing of the delivery apparatus shown in FIG. 1.
Figure 7:
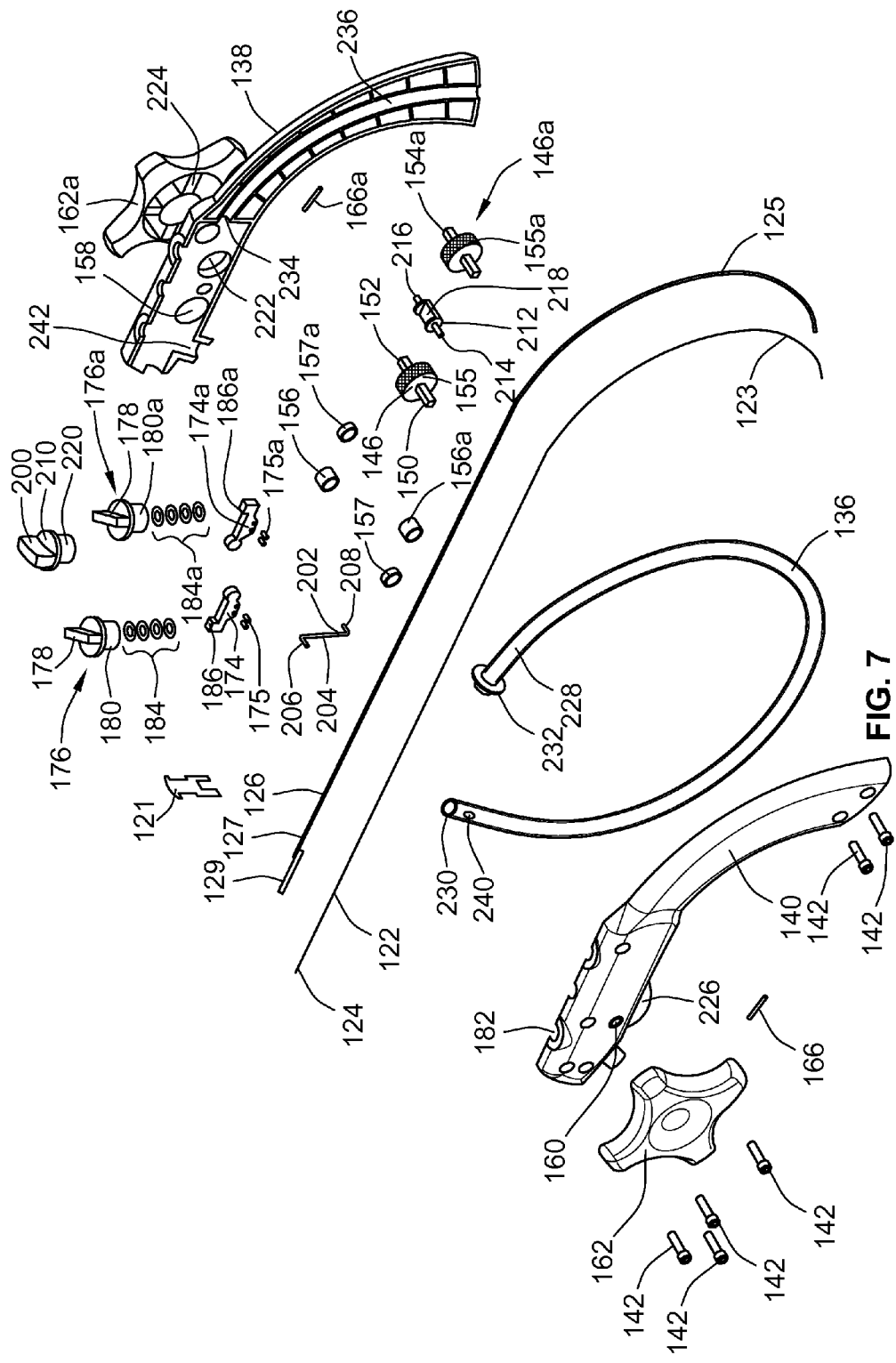
FIG. 7 is an exploded perspective view of the housing shown in FIG. 6.

Referring to FIG. 6, a guide wire 122 can be received within housing 102 and can be advanced from and retracted into the housing 102 by a drive mechanism, which will be discussed in more detail below. The guide wire 122 can be comprised of a variety of materials, such as metal, for example stainless steel, metal alloy or plastic. Referring to FIG. 7, the guide wire 122 has a proximal end portion 123 and a distal end portion 124. In one embodiment, at least the distal end portion 124 of the guide wire is comprised of a shape memory material, such as Nitinol or other suitable shape memory material, such as a shape memory polymer, that has a natural or pre-set shape. As the guide wire 122 is advanced through the delivery cannula 106, the delivery cannula constrains the guide wire 122 in a generally elongated substantially linear configuration, allowing the guide wire 122 to be translated through the cannula 106. As explained in more detail below, because of the shape memory properties, the guide wire 122 will return to its preset shape once the constraint is removed, i.e., as the guide wire 122 exits the distal end portion 110 of the cannula 106.

The housing 122 also can receive pusher member 126. The pusher member 126 is operatively connected to the guide wire 122 such that the pusher member 126 can be selectively advanced out of the housing 102, along the guide wire 122 to push, advance or otherwise navigate or translate an implant along the guide wire 122. As discussed in more detail below, the pusher member 126 can be driven into and out of the housing with a drive mechanism. In the embodiment illustrated in FIG. 7, the pusher member 126 is preferably, but not necessarily, a wire, thread, ribbon, cable, rod or bar. The pusher member 126 has a proximal end portion 125 and a distal end portion 127. Referring to FIGS. 6 and 7, a ferrule (or foot or barrel) 129 is located at the distal end portion 127 of the pusher member 126. The ferrule 129 can be attached to the pusher member 126 by, for example, soldering, or the ferrule and pusher member can be a single piece. The ferrule 129 may have a tubular-like shape with a passage therethrough that receives the guide wire 122 so that ferrule 129 is slidable along or over the guide wire. The ferrule 129 can be flexible or substantially rigid, depending on the procedure and configuration of the guide wire. In one embodiment, the ferrule 129 is constructed of a metal tube that has a spiral cut pattern therealong. The spiral cut pattern allows the ferrule to have sufficient rigidity to push the implant along the guide wire and sufficient flexibility to follow the contour of the flexible bridge 104 and any tortuous path in the delivery cannula 106. In an alternative embodiment, the ferrule 129 is long and constructed of a flexible material (such as a polymer) and is without the spiral cut. In yet another embodiment, the ferrule is very short and therefore does not require a spiral cut. The pusher member 126 is of sufficient length such that it can fully advance an implant of selected length into the treatment site.

Figure 3:
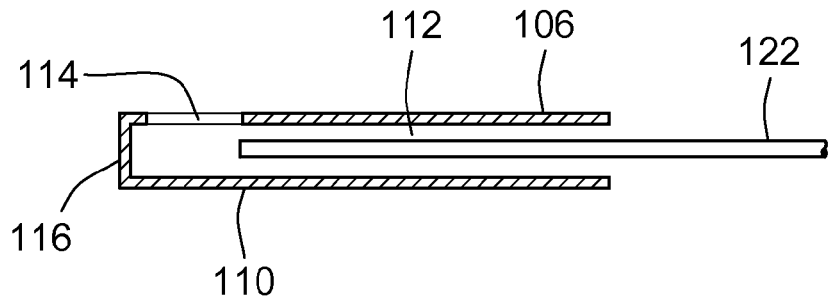
FIGS. 3-5 are cross-sectional views of the distal end portion of the delivery cannula of FIG. 2, which show an exemplary delivery sequence of a guide wire and an implantable medical device from the distal end portion of the delivery cannula.
Figure 4:
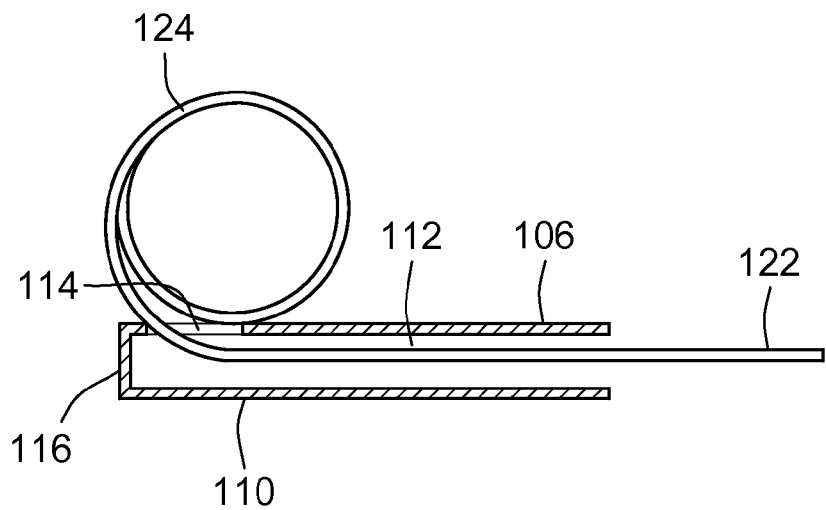
Figure 5:
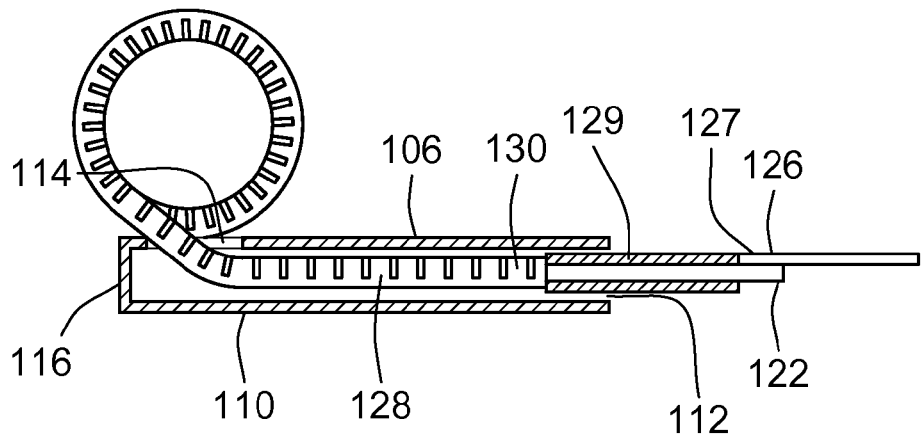

FIGS. 3-5 illustrate the deployment of a guide wire 122 and an implantable medical device 128 out of the distal end portion 110 of delivery cannula 106. Referring to FIG. 3, a guide wire 122 is advanced through interior lumen 112 toward the distal end tip 116 of cannula 106. As illustrated in FIG. 4, the guide wire 122 is advanced through and out of the opening 114 of cannula 106. In the embodiment shown, the guide wire 122 has a linear or straight configuration as it is located in and passes through interior lumen 112 of the cannula 106. Upon exiting the cannula 106, the distal end portion 124 of the guide wire 122 may transition into an arcuate shape, such as the illustrated helical configuration (the preset shape). The cannula 106 can deploy guide wires that have a generally straight configuration (i.e. straightened) for advancement through the cannula and virtually any configuration, such as straight, zigzag, helical or otherwise curved configurations upon exiting the cannula.

Referring to FIG. 5, after the desired amount of guide wire 122 has been deployed from delivery cannula 106, the pusher member 126 is employed to navigate an implantable medical device 128, such as a prosthetic, along or over the guide wire 122. In the illustrated embodiment, as the pusher member 126 is advanced in a distal direction, the ferrule 129 of the pusher member 126 contacts the proximal end 130 of the implant 128 and pushes or otherwise navigates the implant 128 over guide wire 122. After implant 128 is in the desired location, the pusher member 126 and guide wire 122 can be independently or simultaneously retracted back through the cannula 106 or the pusher member 126 can be retracted and the guide wire can be severed.

Figure 1A:
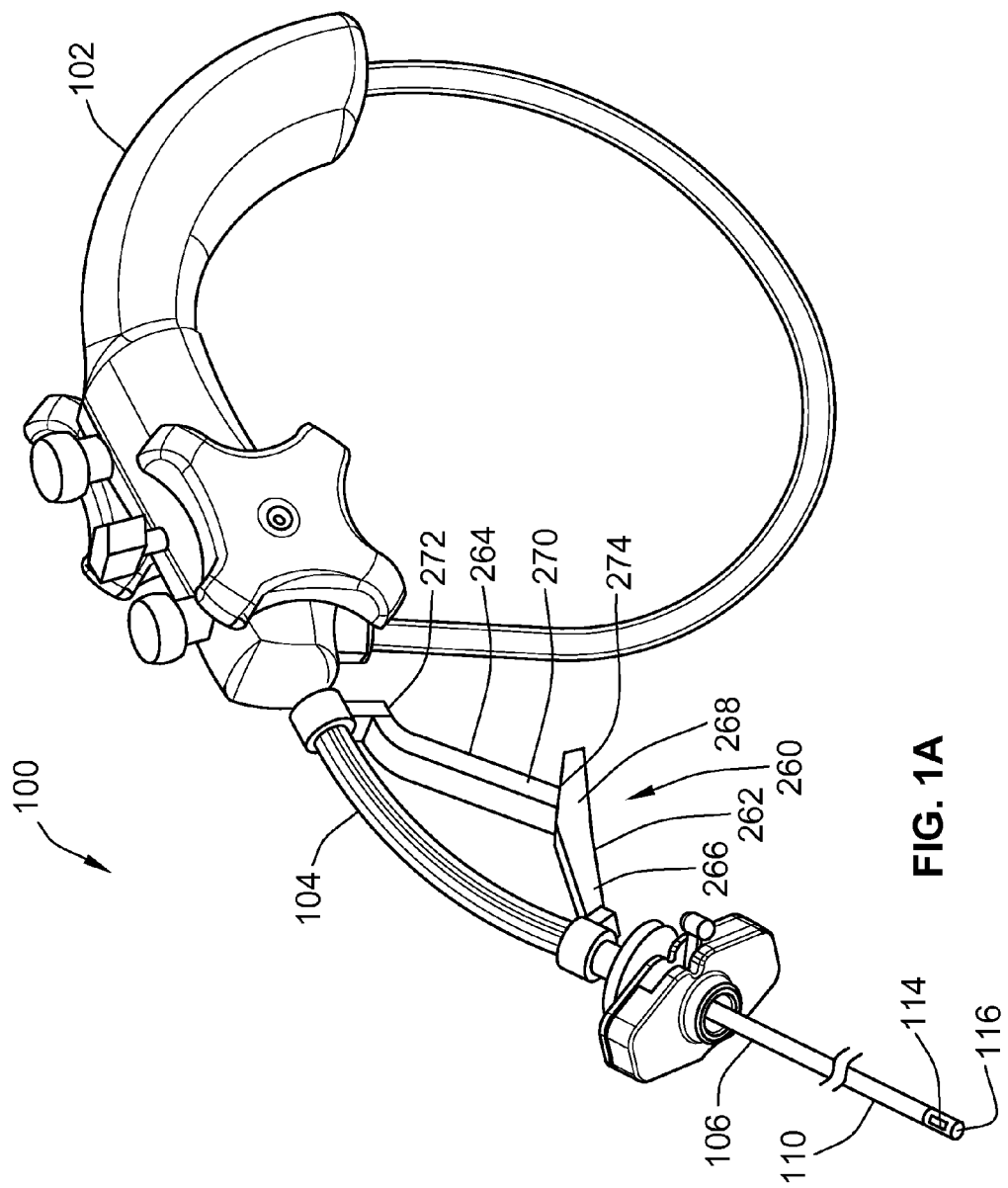
FIG. 1A is a perspective view of another embodiment of a delivery apparatus including a straightener attached to the flexible or bridge member and shown with the straightener in a bent configuration and the flexible or bridge member in a curved configuration.

After the implant has been placed in the desired location and the guide wire 122 is being retracted from the implant and back into cannula 106, there may be instances in which an elevated level of friction arises between the guide wire and the implant. Such elevated levels of friction may be caused by, for example, compression forces placed on the implant or coagulation of blood between the guide wire and the implant. When there is an elevated level of friction and the flexible bridge 104 is curved, as shown in FIG. 1A, the contact between the guide wire and the internal surface of the curved flexible bridge 104 can create additional fiction or drag, which may make it more difficult than desired to retract the guide wire from the implant. To reduce the friction or drag between the curved flexible bridge 104 and the guide wire, the delivery apparatus 100 may optionally include a friction reducing member, such as straightener 260, which may be deployed to place and maintain flexible bridge 104 in a substantially straight or linear configuration. When the flexible bridge 104 is in a substantially straight configuration, the frictional drag between the guide wire and flexible bridge 104 is significantly reduced, thereby reducing the amount of force required to retract the guide wire from the implant.

Figure 1B:
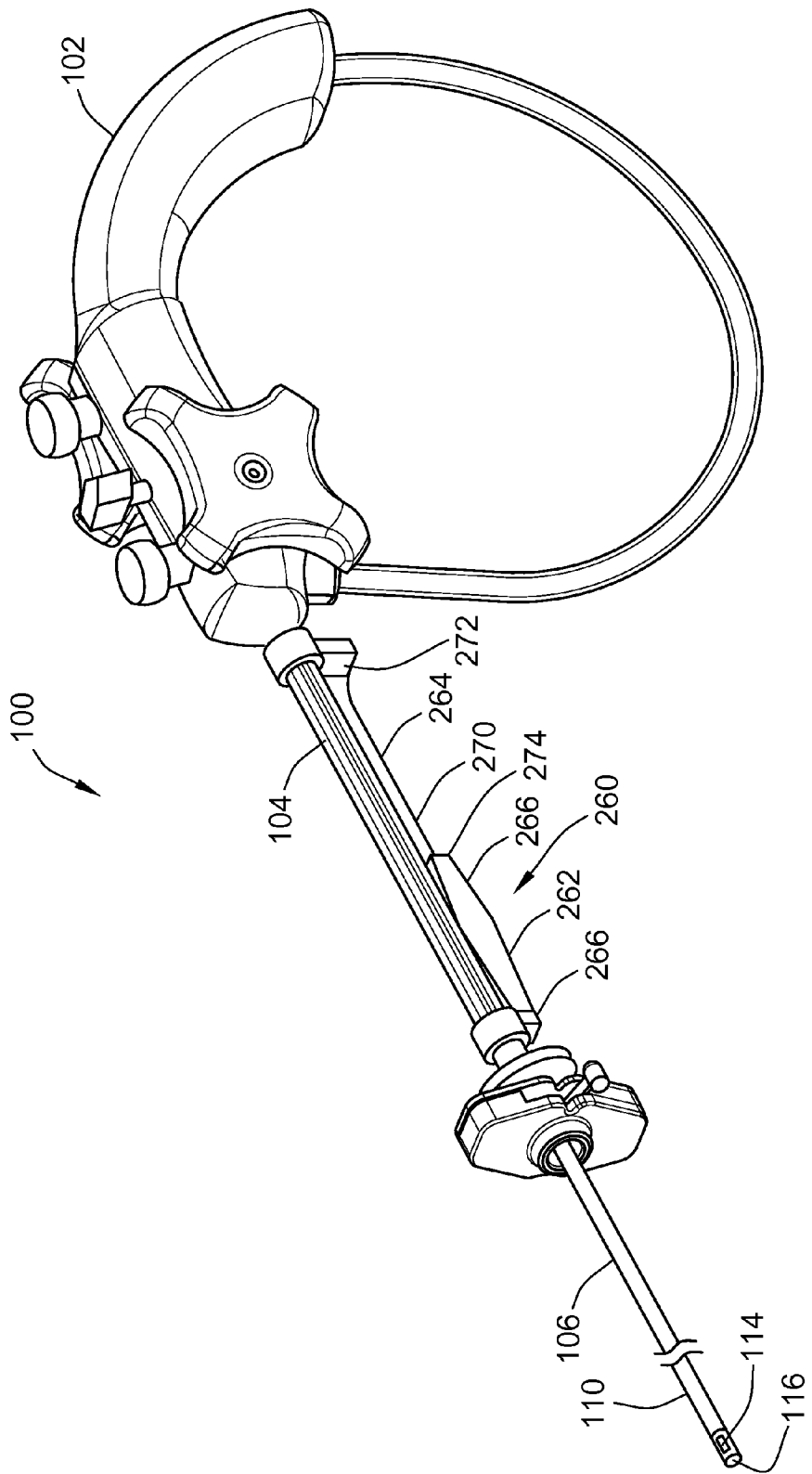
FIG. 1B is a perspective view of the delivery apparatus of FIG. 1A shown with the straightener and flexible or bridge member in a substantially straight configuration.

In the embodiment shown in FIGS. 1A and 1B, the straightener 260 has a plurality of pivotally connected members or legs. For example, the straightener may include a first leg 262 and a second leg 264. The first leg 262 has a distal end portion 266 and a proximal end portion 268. Likewise, the second leg 264 has a distal end portion 270 and a proximal end portion 272. The proximal end portion 268 of first leg 262 is pivotally connected to the distal end portion 270 of the second leg 264 at elbow 274. The distal end portion 266 of the first leg 262 is pivotally connected to the distal end portion of flexible bridge 104 and the proximal end portion 272 of second leg 264 is pivotally connected to the proximal end portion of flexible bridge 104. The elbow 274 allows the first and second legs 262 and 264 to be moved between a relatively angled configuration shown in FIG. 1A and the substantially straight configuration shown in FIG. 1B. When the legs 262 and 264 are in the angled configuration, the flexible bridge 104 is allowed to bend or curve to articulate the housing 102 relative to the cannula 106, as described above. When the legs 262 and 264 are in the substantially straight configuration, the flexible bridge 104 is maintained in a substantially linear configuration (or a reduced curvature shape to reduce friction) and is not allowed to bend or curve. To move the straightener 260 from the bent configuration to the straight configuration, the operator pushes on the elbow 274 towards the flexible bridge 104. To move the straightener 260 from the straightened configuration to the bent configuration, the operator pulls the elbow 274 away from the flexible bridge 104.

In alternative embodiments, other straightening elements may be employed, for example, the flexible bridge could include internal shapeable or straightenable wires within the walls of the flexible bridge or other malleable structures. Alternatively, the flexible bridge 104 may include pull-wires that could be placed under tension to straighten the flexible bridge 104. For example, under low tension, the wires would be relaxed and the flexible bridge 104 would be allowed to bend or curve. Under high tension, tension would be placed on the wires to move and maintain the flexible bridge in a substantially straightened (reduced curvature) configuration. The tension could be controlled by, for example, a knob, lever or dial.

Turning to FIG. 6, the housing 102 of delivery apparatus 100 is preferably, but not necessarily, configured to be handheld so that the user can manually facilitate control and positioning of the cannula 106 during use. The housing 102 preferably is constructed from any suitable material, such as stainless steel, plastic or the like. In the illustrated embodiment, the housing 102 generally defines a body portion 132, a handle portion 134 and a receptacle 136. Preferably, the handle portion 134 is sized and shaped for convenient holding by a physician. In the embodiment shown, the handle portion 134 has a curved shape; however, other configurations or contours of the handle, preferably those that provide for ergonomic convenience, may also be used. The handle portion 134 may also include additional features to aid the user's grip, such as gripping material or finger grooves.

As illustrated in FIG. 7, the housing 102 can include two halves, a right half 138 and a left half 140, which are affixed together to form the housing 102. In the illustrated embodiment, the right and left halves 138 and 140 are fastened together by screws 142. The halves 138 and 140 can also be fastened together by other suitable means, such as with an adhesive, mechanical fastener, solvent, or polymeric molecular bond.

Figure 7A:
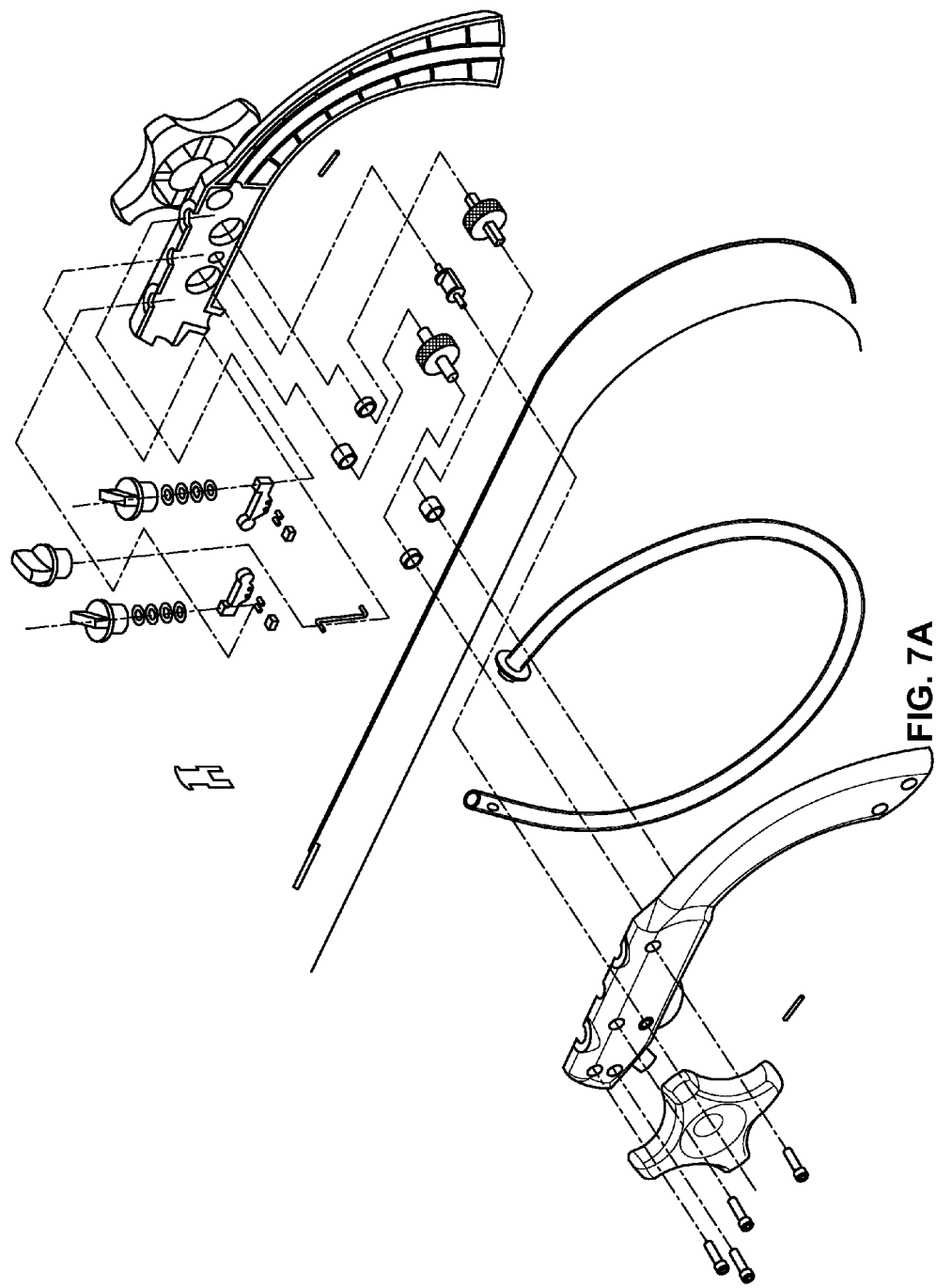
FIG. 7A is an exploded perspective view of the housing of FIG. 7 shown with projection lines.
Figure 8:
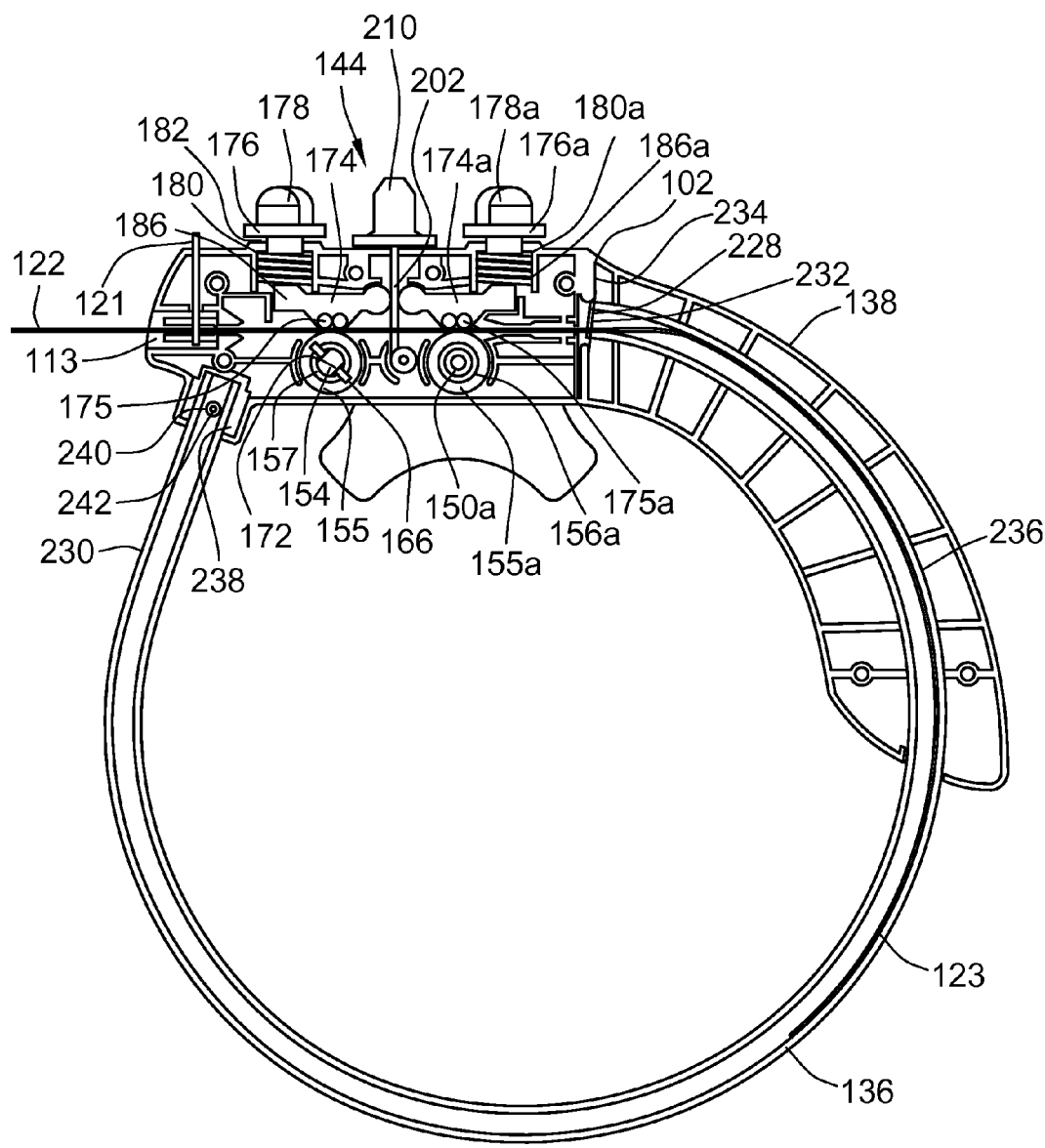
FIG. 8 is a cross-sectional view of the housing shown in FIG. 6.

Referring to FIGS. 7, 7A and 8, the body portion 132 of housing 102 can house a drive mechanism 144 that is shown in an exploded view in FIGS. 7 and 7A and an assembled view in FIG. 8. The drive mechanism 144 is used to advance and retract the guide wire 122 and pusher member 126 out of and into the housing 102. The drive mechanism 144 can be at least partially positioned within the body portion 132 of the housing 102. In the embodiment shown, the drive mechanism 144 includes first and second drive elements 146 and 146a which are positioned one in front of the other. The first drive element 146 is utilized to selectively advance and retract the guide wire 122. The second drive element 146a is utilized to selectively advance and retract the pusher member 126. Additionally, the first and second drive elements 146 and 146a may be slightly offset from each other so that the guide wire 122 and pusher member 126 can be driven in the side-by-side orientation that is shown in FIG. 6.

As shown in FIG. 7, the first drive element 148 includes a rotatable drive shaft 150. The drive shaft 150 can be constructed of a very hard material, such a metal, and includes a first end portion 152 and a second end portion 154 with a wheel or hub portion 155 therebetween. To reduce rotational friction, a sleeve 156 may be located over the first end portion 152 of the drive shaft 150. The sleeve 156 and the first end portion 152 are supported by cavity 158 of the right halve 138 of housing 102. The second end portion 154 of the drive shaft 150 may receive a sleeve 157 thereover, and the second end portion 154 is inserted through and supported by opening 160 located in the left halve 140 of the housing 102. The sleeves 156 and 157 can be standard or custom bearings to assist in providing smooth rotation of the drive shaft 150.

The second end portion 154 of drive shaft 150 extends out of opening 160 of left body half 140, and a rotating mechanism, such as drive knob 162, is attached to the second end portion 154. In the embodiment shown, the drive knob 162 is mechanically connected to the second end portion 154 of drive shaft 150. For example in the illustrated embodiment, the second end portion 154 may be inserted into a central cavity 164 (FIG. 9) located on the inside of the drive knob 162. To secure the drive knob 162 to the second end portion 154, a pin 166 (FIGS. 7 and 8) is inserted through walls 168 and 170 of the drive knob 162 (FIG. 9) and a hole 172 (FIG. 8) in the second end portion 154 of the drive shaft 160. In other embodiments, the end portions can be pressed in, snapped in, pinned, etc. to the drive knob. Turning drive knob 162, preferably by hand, will rotate the drive shaft 150. The wheel portion 155 of the drive shaft 150 frictionally engages the guide wire 122 and drives the guide wire as the drive shaft 150 rotates. In the illustrated embodiment, the drive shaft 150 advances the guide wire 122 out of the housing 102 when drive knob 162 is rotated in a counterclockwise direction and retracts the guide wire into the housing when rotated in a clockwise direction.

Figure 10:
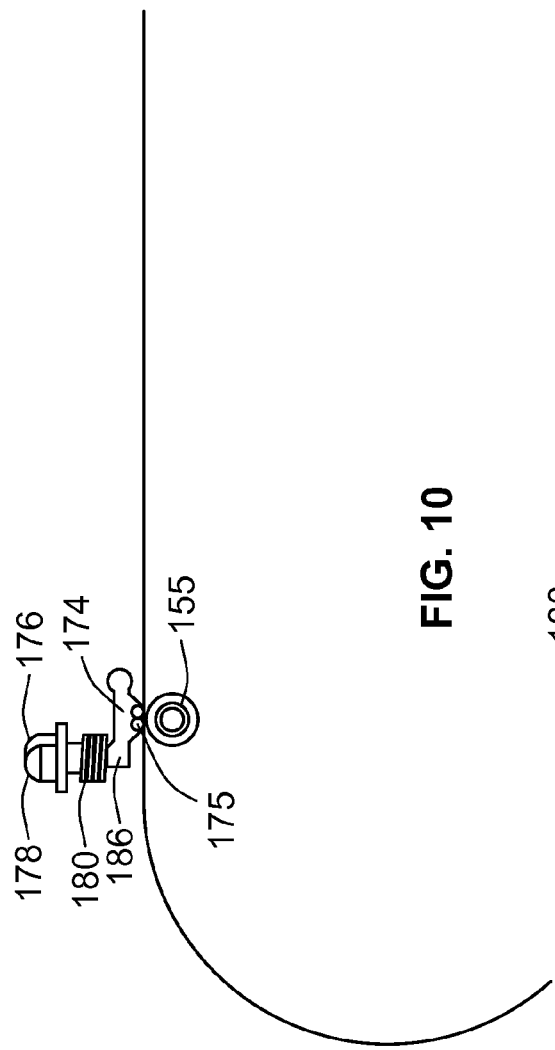
FIG. 10 is a schematic illustration of one embodiment of a drive mechanism constructed in accordance with the present disclosure.

As illustrated in FIGS. 8 and 10, a compression member 174 supported by the housing 102 may be positioned above the wheel portion 155 of the drive shaft 150. When utilized, the compression member 174 is spaced from the wheel portion 155 such that guide wire 122 is sandwiched or pinched between the compression member 174 and outer surface of the wheel portion 155. The amount of compressive force exerted by the compression member 174 is variable and can be adjusted by turning a compression knob 176. The compression knob 176 includes a gripping portion 178 and a shaft 180. The gripping portion 178 of the knob 174 is positioned exterior to the housing 102. The shaft 180 is received into a slot 182 defined by the housing 102. The shaft 180 and the slot 182 are complementarily threaded, so that the shaft 180 moves into and out of the slot 182 as the knob 176 is rotated. Preferably, a compression spring 184 (FIG. 7) resides in the shaft 180 of the knob 176 and interacts with an arm 186 of the compression member 174. In the embodiment shown, the compression spring 184 includes a plurality of compression washers. When rotated in a first direction, the shaft 180 of the knob 176 moves into the slot 182 of housing 102 and the spring 184 inside the shaft 180 applies a force or increases the force applied to arm 186 of compression member 174, which causes an increase in the compression load placed on the portion of the guide wire 122 between the compression member 174 and the wheel portion 155. Conversely, the knob 176 may be rotated in the opposite direction to decrease the compression load placed on the portion of the guide wire 122 pinched between the wheel 155 and compression member 174.

The compression member 174 places a compression load on the guide wire 122 to increase the friction between the guide wire 122 and wheel portion 155 of the drive shaft 150. There should be sufficient friction between the guide wire 122 and wheel portion 155 so that the guide wire 122 advances or retracts as the wheel portion 155 rotates. Additionally, the wheel portion 155 of the drive shaft 150 can include teeth or ridges on the outer surface. The wheel portion 155 can be what is sometimes referred to as a knurled wheel. Under the compressive load provided by the compression member 174, the teeth grab the guide wire 122 to advance it or retract it. Optionally and when the compressive force is large enough, the teeth can create small indentations or rack teeth in the guide wire 122. The rack teeth assist the wheel 155 in gripping the guide wire 122 for advancement and/or retraction. To facilitate the creation of rack teeth in the guide wire 122, the teeth of wheel 155 can be sharp, pointed or otherwise shaped.

When the guide wire 122 is to be inserted into certain tissue, such as cancellous bone tissue of a vertebral body, the advancement force required for such insertion can be about 50 $lb_f$ (about 222 N). In order to obtain such an advancement force, the pinch force on the guide wire 122 between the compression member 174 and the wheel portion 155 can be required to be relatively large, which results in a substantial amount of friction between the compression member 174 and the guide wire 122. Under certain conditions, such friction can encourage the guide wire 122 to remain static and may make it relatively difficult to rotate to the drive shaft 150. In order to reduce friction between the guide wire 122 and the compression member 174, the compression member 174 may include one or more rolling pins 175 (FIGS. 7, 8 and 10). As the guide wire 122 is driven by the drive shaft 150, the rolling pins 175, which are fictionally engaged with guide wire 122, rotate within the compression member 174, reducing the friction between the guide wire 122 and the compression member 174. The compression member 174 can include one rolling pin or a plurality of rolling pin 175 and, in the illustrated embodiment, the compression member 174 includes a pair of rolling pins 175. The rolling pins 175 can be positioned to force the guide wire 122 or pusher wire to flex in an arc around the wheel portion 155 of drive shaft 150 to maintain a maximum length of engagement. Additionally, the friction that results from compression of the wire against the wheel portion 155 of drive shaft 150, while in the static and dynamic states, can provide a braking action that may prevent accidental or self-propelled ejection of the guide wire 122.

Figure 10A:
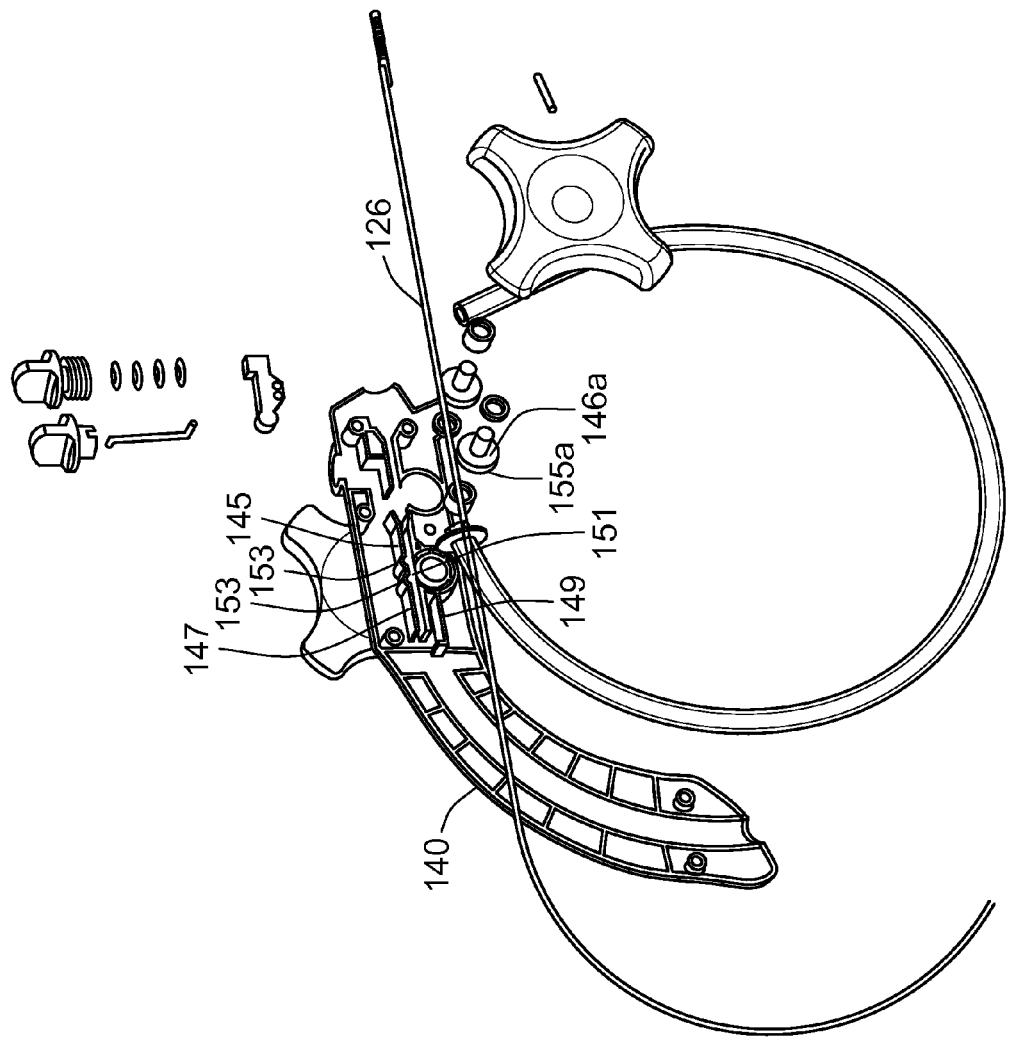
FIG. 10A is an exploded view of the left housing half including another embodiment of a drive mechanism.

FIG. 10A illustrates another embodiment of a drive mechanism. The drive mechanism is shown and described in connection with driving of the pusher member 126, but it will be understood that the same or a generally similar drive mechanism also may be utilized to drive the guide wire. In the illustrated embodiment, the left housing half 140 includes a channel 145 that is located above the drive mechanism 146a, when the delivery apparatus is assembled. The channel 145 is defined by a top wall 147 and a bottom wall 149. The channel 145 receives the pusher member 126 and allows passage of the pusher member therethough. The bottom wall 149 of the channel 145 includes an opening 151 that allows the wheel portion 155a of the drive member 146a to extend into the channel 145, when the housing is assembled. Optionally, the right housing halve may include a corresponding channel having a similar structure. When the housing is assembled, the channels of the left and right housing mate to create a passageway for the pusher member.

When the pusher member 126 is driven, it passes through the channel 145. The distance between the top wall 147 of the channel 145 and the wheel portion 155a of the drive member 146a is such that the pusher member 126 is pinched between the top wall 147 and the wheel portion 155a. The pinching of the pusher member 126 results in load being placed on the wire toward the wheel portion 155a to create a frictional engagement between the pusher member 126 and the wheel portion 155a. There should be sufficient frictional engagement between the pusher member 126 and the wheel portion 155a so that the pusher member 126 is driven when the wheel portion 155a is rotated. Preferably, the channel 145 has a tight tolerance with the pusher member 126. Also, the amount of friction created between the wheel portion 155a and the pusher member 126 may be adjusted by varying the tolerance of the channel 145 and the distance between the wheel portion 155a and the top wall 147.

In one embodiment, the pusher member 126 may have a rack that engages pinions of the wheel portion 155 of drive member 146. In another embodiment, the pusher member 126 has a rack that extends along substantially the entire length of the pusher member. Optionally, the top wall 147 of channel 145 may also include slots 153 that receive rollers or dowels (not shown). The rollers may be utilized to create a higher pinching force. Additionally, as the pusher member 126 is driven, the rollers rotate so as to reduce friction between the top wall 147 and the pusher member 126, which reduces the amount of rotational force required to drive the pusher member.

Figure 11:
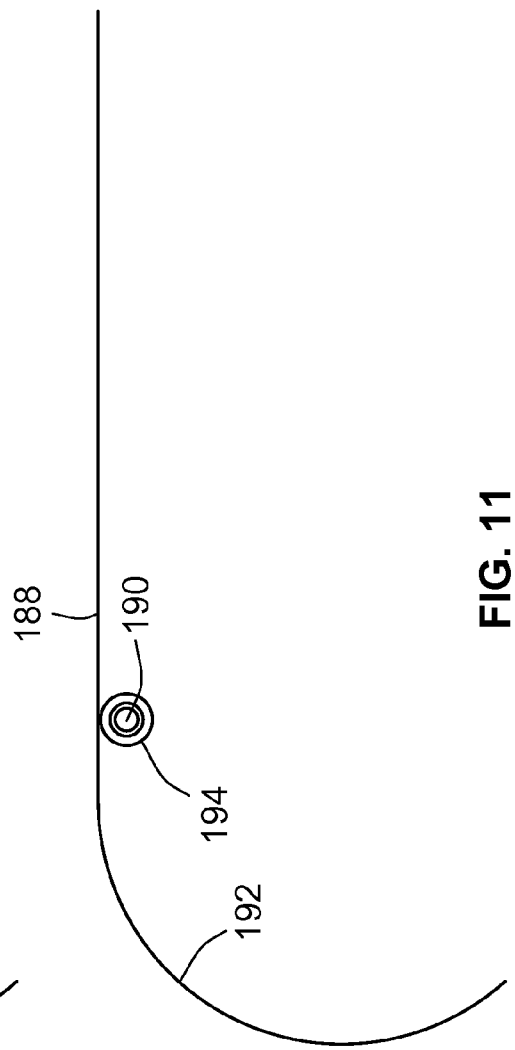
FIG. 11 is a schematic illustration of an other embodiment of a drive mechanism constructed in accordance with the present disclosure.

FIG. 11 illustrates an alternative embodiment of a guide wire 188 and drive shaft 190 that does not require a high pinch force, and thus, does not require a compression member to provide a large compressive load on the guide wire. In this embodiment, the guide wire 188 includes rack teeth 192, preferably deep rack teeth, that engage pinion teeth (not shown) located on the wheel 194. The guide wire 188 is constrained within the housing, by the structure of the housing or otherwise, so that rack teeth 192 and pinion teeth are in engagement with each other to advance or retract the guide wire 188 as the wheel 194 is rotated.

The second drive element 146a, second drive knob 162a and second compression member 174a and their interrelationship are substantially identical to the first drive element 148, first drive knob 162 and first compression member 174 discussed above, except that the second drive member 146a is utilized to advance and retract the pusher member 126. Thus, the features and components of the above-mentioned elements will not be described herein and like elements will be designated with like reference numbers followed by the designation "a."

Figure 9:
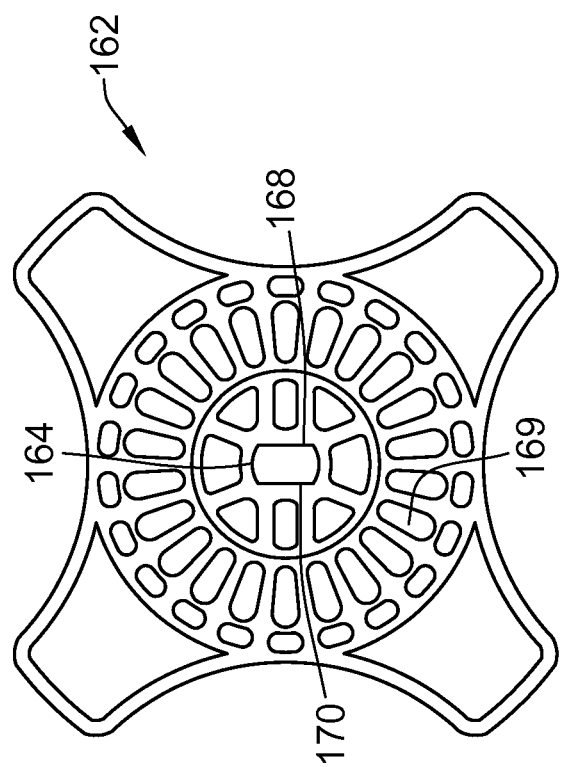
FIG. 9 is an enlarged view of one of the drive knobs of the delivery apparatus of FIG. 1.

In order to selectively control the movement of the first or second drive elements 146 and 146a, the housing 102 may include a drive switch 200, which selectively allows movement of one drive element while preventing movement of the other drive element. In the illustrated embodiment, the drive switch 200 is located between drive knobs 162 and 162a. Referring to FIGS. 7 and 8, the drive switch 200 includes a generally Z shaped bar 202 (referred to herein as "Z" bar) that has a spindle 204 with a top arm 206 and a bottom arm 208 extending from the spindle. The "Z" bar 202 operatively connects a switch knob 210, which is rotatably mounted on the body 132, to a toggle 212. The toggle includes a first pin 214, a second pin 216 and a well 218 therebetween. The top arm of 206 of the "Z" bar 202 engages a slot 220 of switch knob 210, and the bottom arm 208 of the "Z" bar 202 engages well 218 of toggle 212. The switch knob 210, "Z" bar 202 and toggle 212 are assembled so that when the front of the switch knob 210 is rotated in a counterclockwise direction toward the drive knob 162, the "Z" bar 202 rotates about the longitudinal axis of the spindle 204 and the engagement between the bottom arm 208 of the "Z" bar 202 and the well 218 of the toggle 212 causes the toggle 212 to move perpendicular to the longitudinal axis of the spindle in a direction toward drive knob 162a. When in this position, the second pin 216 of the toggle 212 extends through opening 222 in the right housing half 138 and engages a cavity 224 of the drive knob 162a. The engagement between the second pin 216 and the drive knob 162a prevents rotation of the drive knob 162a. Additionally, when the toggle 212 is in this position, the first pin 214 is retracted into opening 226 of left housing half 140, and drive knob 162 is free to be rotated by the user. Conversely, when the front of the switch knob 210 is rotated in a clockwise direction toward the drive knob 162a, the toggle 212 moves toward drive knob 162. When the toggle 212 is in this position, the first pin 214 extends out of opening 226 of left housing half 140 and into engagement with a cavity 169 of drive knob 162 (FIG. 9). Thus, drive knob 162 is prevented from rotating and drive knob 162a is free to be rotated by the user.

Referring to FIG. 8, when the guide wire 122 and pusher member 126 (not shown in FIG. 8), are received into or retracted into housing 102, the proximal end portion 123 of the guide wire 122 and the proximal end portion of the pusher member 126 are received into receptacle 136, if one is present. Receptacle 136 houses, protects and controllably contains the guide wire 122 and pusher member 126. In the embodiment illustrated in FIGS. 7 and 8, the receptacle has an elongated tubular shape and a generally curved configuration. The function of this receptacle may also be present as part of the handle, eliminating the need for a separate component. Receptacle 136 also includes a first end 228 and a second end 230. The first end 228 extends into housing 102 and is generally aligned with wheel portions 155 and 155a of drive shafts 150 and 150a. In this position, the guide wire 122 and pusher member 126 are fed into the receptacle 136 when they are retracted by the drive mechanism. The first end 228 includes a circumferential extension 232 extending radially outward from the first end 228 portion of the receptacle 136. The circumferential extension 232 can be a toothed lock washer slid over the end 228 receptacle 136. The circumferential extension 232 is trapped between the body halves 138 and 140 of the housing 102 and abuts inner wall 234 of the housing 102 to secure the receptacle to the housing. Additionally, the receptacle can pass through and follow the contour of the handle portion 134. Each half 138 and 140 of the handle portion 134 can include a channel 236 in which the receptacle 136 resides. The second end 230 of the receptacle is located in opening 238 of the housing 102. The second end 230 includes an opening 240 therethrough and a post 242, projecting from either half 138 and 140 of the housing 102. The post 242 extends through the hole 240 to attach the second end 230 of the receptacle 136 to the housing 102.

FIGS. 12-16 illustrate the loading of an implantable device 128 into the delivery apparatus 100 (FIG. 1). The delivery apparatus 100 can be pre-loaded or can be loaded by the surgeon prior to the treatment procedure. Referring to FIG. 12, the guide wire 122 is partially inserted or located in delivery cannula 106. The implantable device 128 is inserted over or along the guide wire 122, and optionally, partially within the delivery cannula 106. Turning to FIG. 13, the proximal end 123 of the guide wire 122 is inserted into the flexible bridge member 104, and the flexible bridge member is slid over the guide wire 122 and the implantable device 128. The distal end portion 105 of the flexible bridge member 104 is inserted into attachment member 118 of the delivery cannula 106. The flexible bridge member 104 is then secured to the delivery cannula 106 by moving lock lever 120 (FIG. 12) to the locked position. Turning now to FIG. 14, the proximal end portion 123 of the guide wire 122 is then inserted into the ferrule 129 of the pusher member 126 and fed into the drive mechanism. Referring to FIGS. 15 and 16, the flexible bridge member 104 is then slid over the pusher member 126. The proximal end portion 107 of the flexible bridge member 104 is inserted into the housing 102 and attached housing with a lock clip 121. The drive knob 162 is then turned to retract the guide wire 122 into the housing 106. As the guide wire 122 is retracted, the proximal end portion 123 of the guide wire 122 is received into receptacle 136 (FIG. 8). The guide wire 122 and implantable device 128 are now loaded into the delivery apparatus 100 and ready for use.

Figure 17:
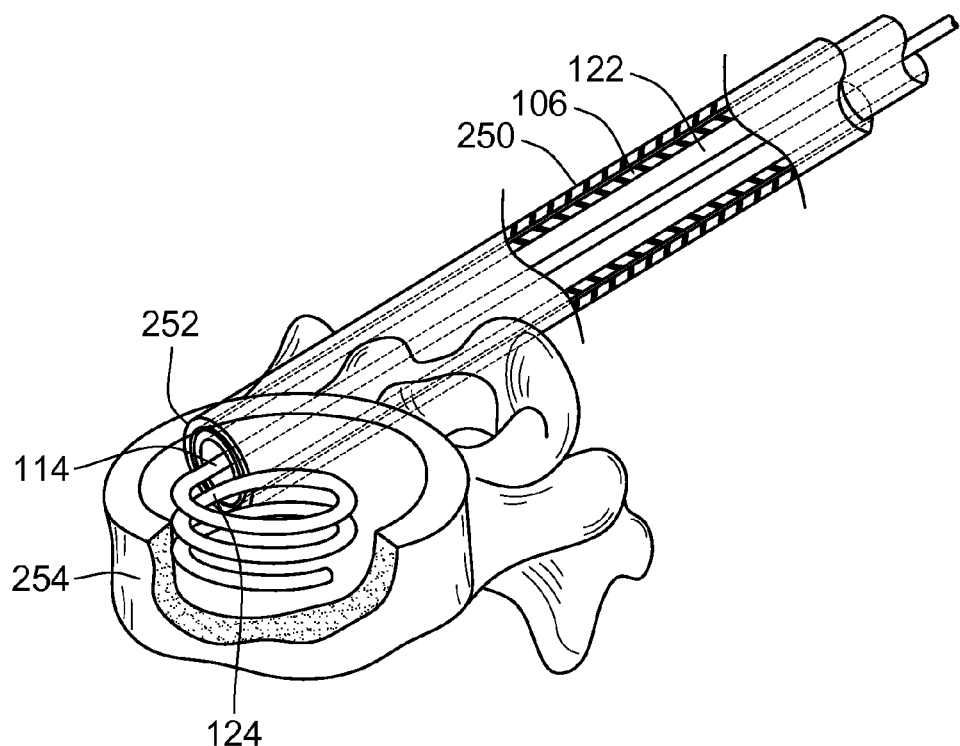
FIGS. 17 and 18 are perspective views of a vertebra, showing the delivery of a guide wire and implantable device from the delivery cannula.
Figure 18:
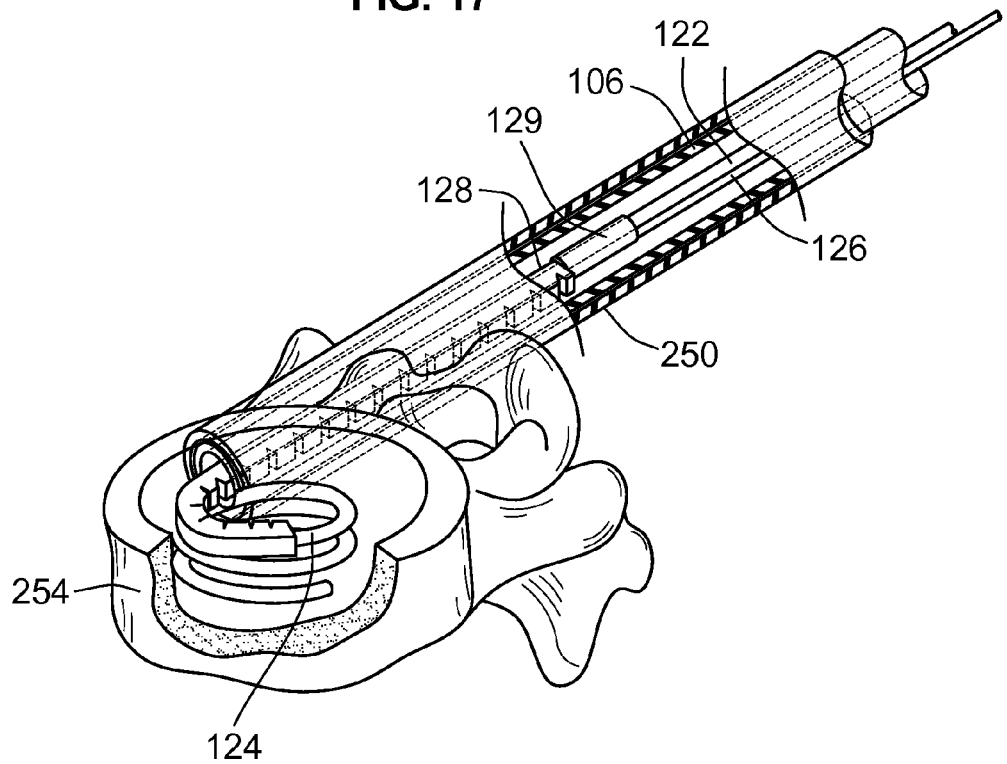

FIGS. 17 and 18 illustrate one exemplary use of the delivery apparatus of the present disclosure. An introducer sheath or working cannula 250 is introduced through the back of a patient preferably while the patient is lying in a prone position. Fluoroscopic guidance using a biplane imaging system for better visualization of the spine may be used to help guide the working cannula 250 to the desired location. Working cannula 250 can be introduced through an access port 252 in the vertebral body 254 using a transpedicular access approach. Once working cannula 250 is in the desired position, the delivery cannula 106 is inserted into working cannula. Switch knob 210 (FIG. 8) is then turned counterclockwise toward drive knob 162, and the drive knob 162 (FIG. 7) is rotated to advance the guide wire 122. As illustrated in FIG. 17, the guide wire 122, in a straight configuration, is advanced through the delivery cannula 106 and out of an opening 114 in the distal end portion of the cannula 106. In the embodiment shown, as the distal end portion 124 of the guide wire 122 exits the opening 114 it forms into a spiral configuration. Also, in this embodiment, the opening 114 in the distal end portion 110 of the delivery cannula 106 is located at the distal tip of the cannula instead of in the side of the cannula.

Once the guide wire 122 is in the desired location, the switch knob 210 (FIG. 6) is turned in a clockwise direction toward drive knob 162a (FIG. 6) and the drive knob 162a is then rotated to advance the pusher member 126. As illustrated in FIG. 18, as the pusher member 126 is advanced, ferrule 129 advances over the guide wire 122 and contacts and pushes the implantable device 128 along the guide wire 122 and into the vertebral body 254. After the implantable device 126 is in the desired position, the switch knob 210 (FIG. 6) can be rotated back toward the drive knob 162 (FIG. 6). With the pusher member 126 holding the implantable device 128 in place, the drive knob 162 is turned to retract the guide wire 122 from the implant and into the delivery cannula 106. The switch knob 210 once again turned back toward the drive knob 162a and drive knob 162a is rotated to retract the pusher member 126, leaving the implant implanted in the vertebral body 254. It will be understood that the delivery apparatus disclosed herein can be used to deploy a medical implant to other parts of the body as well.

FIGS. 19-23 illustrate an alternative embodiment of a housing 300 and a drive mechanism. The housing 300 includes a right housing half 304 and a left housing half 306, which are joined together to define the housing. The housing halves 304 and 306 can be joined together by fasteners, such as screws, interference fit or by an adhesive, or similar means. Similar to the previous embodiment, a flexible bridge member 104 and delivery cannula 106 can be attached to the housing 300 and a guide wire and pusher member can be driven from the housing 300 through the flexible bridge 104 and cannula 106. Housing 300 includes an opening 308 for receiving the flexible bridge member and a lock-clip 310 (or locking lever or threaded nut) for securing the flexible bridge member to the housing 300 by attachment to the proximal coupling.

Figure 19:
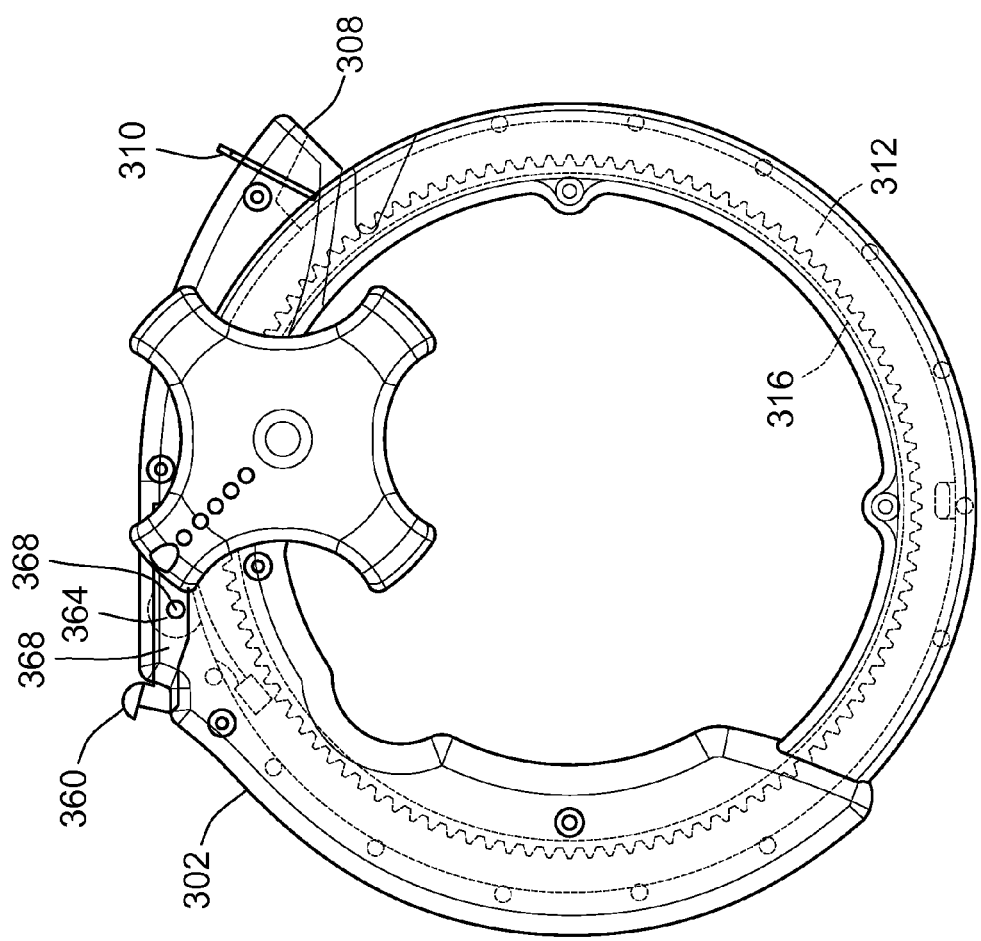
FIG. 19 is a side view of another embodiment of a housing and drive mechanism constructed in accordance with the present disclosure.
Figure 20:
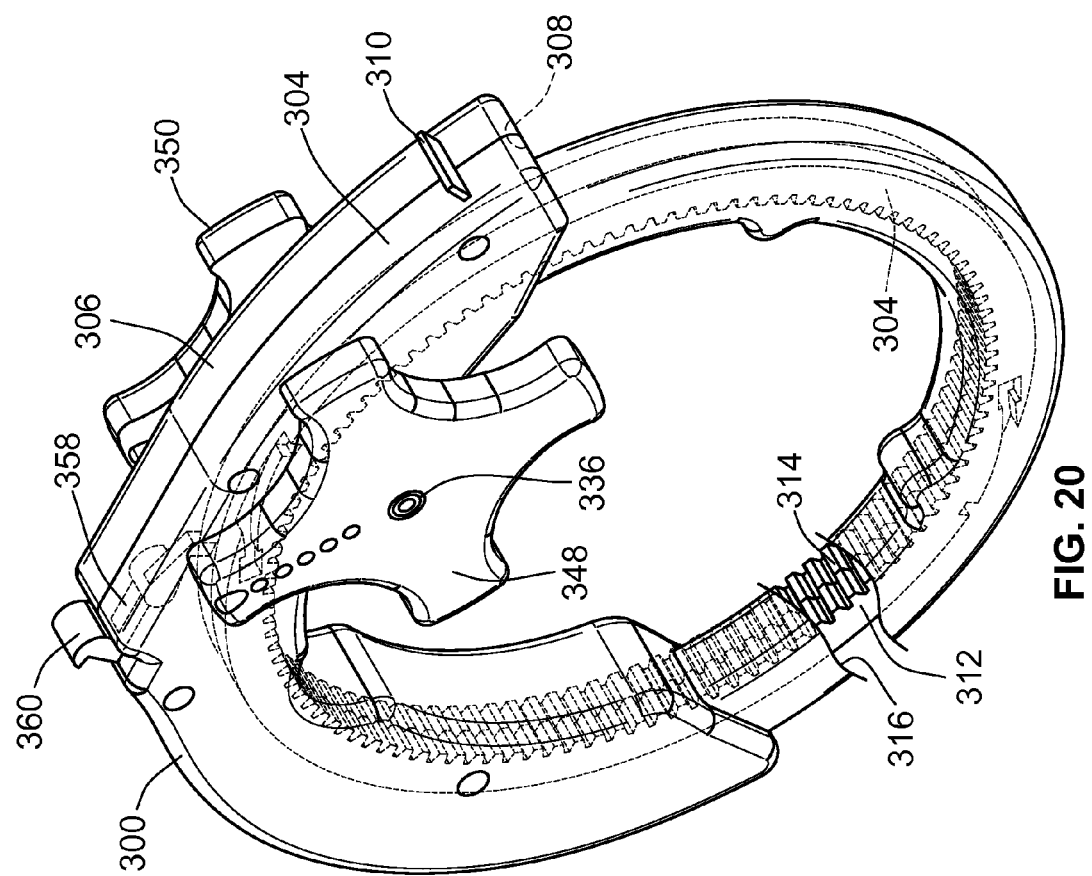
FIG. 20 is a perspective view of the housing shown in FIG. 19.

Referring to FIGS. 19 and 20, the housing 300 has a generally ring-shaped configuration and houses the drive mechanism. An alternative embodiment may include linear travelling rigid or flexible carriages that are manipulated by the handle drive mechanism. The drive mechanism utilizes an internal gear and pinion-type gear assembly and includes a pair of ring-shaped carriages, magazines or spools 312 and 314 that drive the guide wire and pusher member. The carriages 312 and 314 are located within a channel 316 defined by the interior walls of housing 300. The carriages 312 and 314 are rotatable within the channel 316. In one embodiment, the carriages 312 and 314 are rotatable independently of one another. In another embodiment, the carriages 312 and 314 are jointly or simultaneously rotatable.

Figure 21:
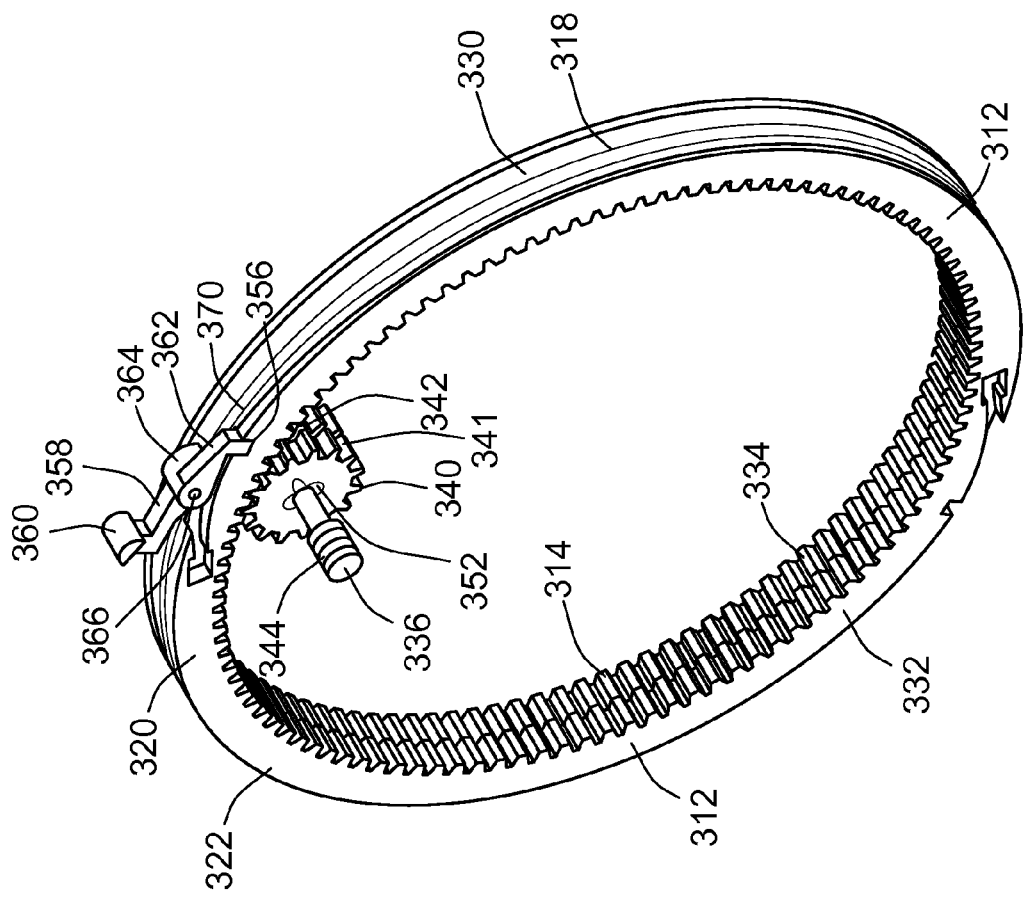
FIG. 21 is a perspective view of the drive mechanism shown in FIG. 19.
Figure 22:
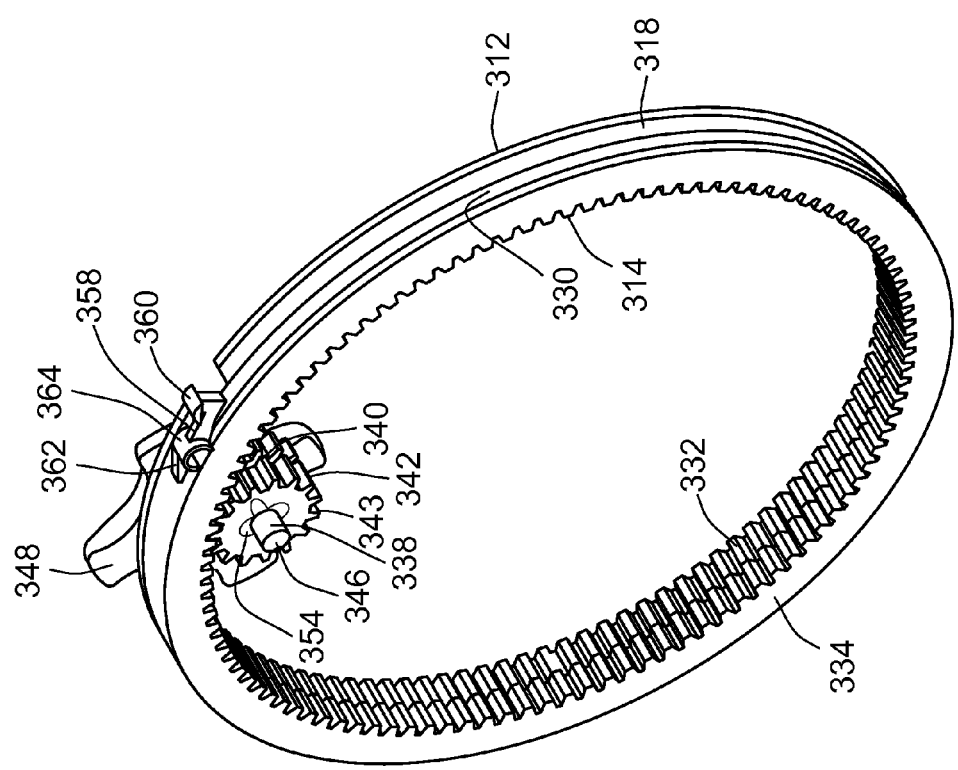
FIG. 22 is another perspective view of the drive mechanism shown in FIG. 19.
Figure 23:
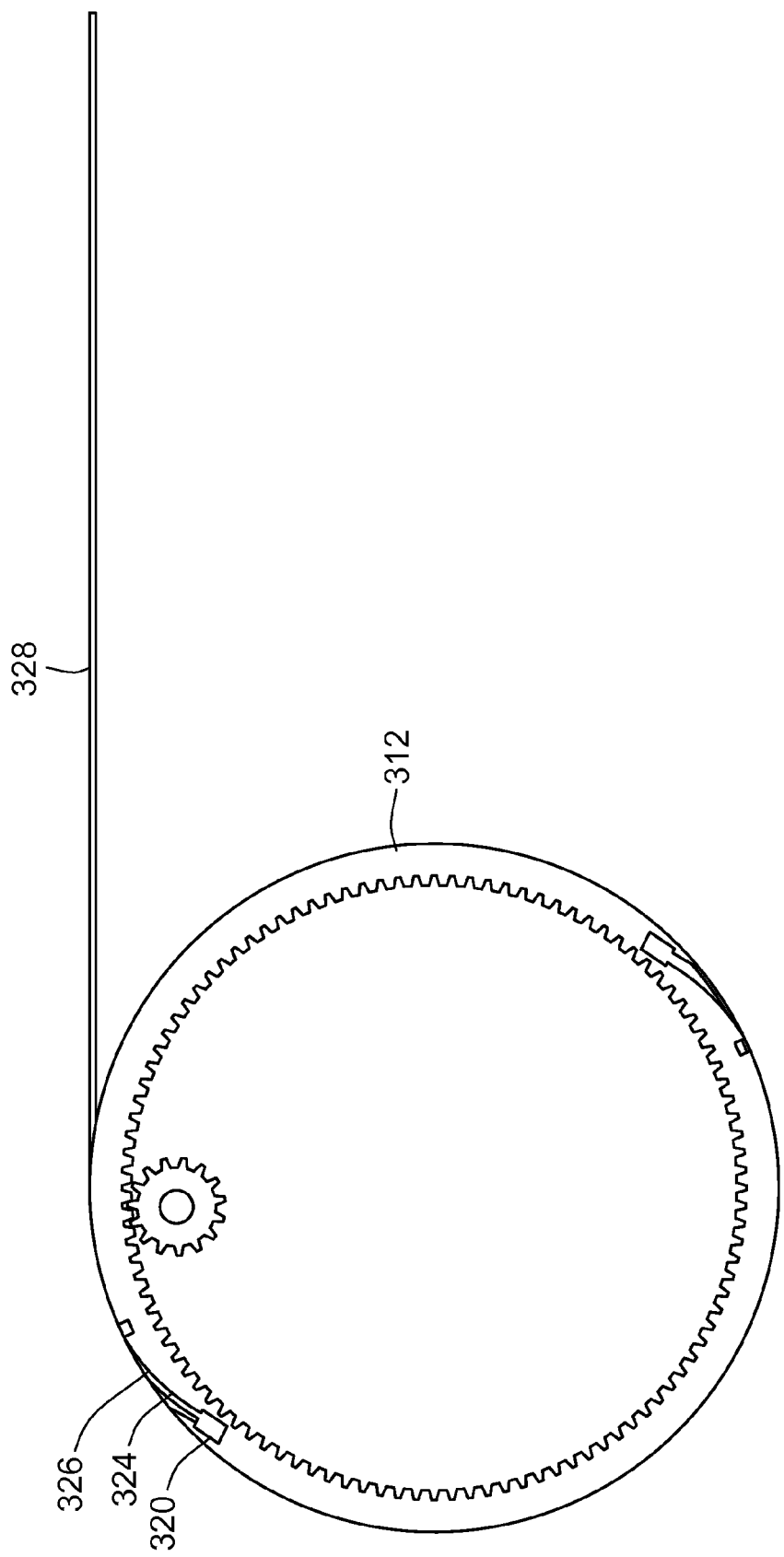
FIG. 23 is a schematic illustration of the drive mechanism shown in FIG. 19.

Turning to FIGS. 21 and 22, carriage 312 includes a channel 318 that extends around the outer circumference of carriage 312. The channel 318 is sized to receive a guide wire (not shown) that is wound around the carriage. Additionally, the proximal end of the guide wire is attached to the carriage 312 to assist in winding and unwinding the guide wire from the carriage as the carriage drives the guide wire. In the illustrated embodiment, the carriage 312 includes a notch 320 located in a sidewall 322 of the carriage. Referring to FIG. 23, the notch 320 receives an enlarged portion 324, such a crimped ferrule, located at the proximal end 326 of the guide wire 328. The enlarged portion 324 is secured or otherwise trapped within the notch 320 of the carriage 312 to secure the proximal end 326 of the guide wire 328 to the carriage 312. The proximal end of the guide wire may be secured to the carriage by a variety of different methods. For example, in one embodiment, the guide wire may have teeth in the proximal end portion or tail that snap into mating teeth in a similar channel in the carriage. In yet another embodiment, the wire has notches in its proximal end, and when the wire is inserted into the retention channel, the notches align with holes in the carriage into which metal dowel pins are inserted.

Carriage 314 is substantially identical to carriage 312 and also includes a channel 330 that extends around the outer circumference of carriage 314. The channel 330 is sized to receive a pusher member (not shown) that is wound around the carriage 314. The carriage 314 also includes a notch (not shown) that receives a proximal end portion of the pusher member to secure the pusher member to the carriage.

Each of the carriages 312 and 314 also include a set or plurality of teeth (which can be considered rack teeth) 332 and 334, respectively, that extends continuously around the inner circumference of the respective carriage 312 and 314. Referring to FIGS. 21 and 22, the drive mechanism also includes a first drive shaft 336 (FIG. 21) operatively associated with carriage 312 and a second drive shaft 338 operatively associated with carriage 314. Each drive shaft 336 and 338 includes a toothed wheel 340 and 342, respectively, (which can be considered pinions) located thereon. Each of the toothed wheels 340 and 342 has a set or plurality of teeth 341 and 343 that is associated and meshes with the rack teeth 332 and 334 of a respective carriages 312 and 314, which also may be considered internal gears. The end portions 344 and 346 of the drive shafts 336 and 338, respectively, extend out of the housing 300 where knob 348 (FIGS. 20 and 22) is attached to end portion 344 (FIG. 21) of drive shaft 336, and drive knob 350 (FIG. 20) is attached to end portion 346 (FIG. 22) of drive shaft 338.

In the embodiment shown, carriage 312 and 314 are independently rotatable with respect to each other. Rotation of drive knob 348 causes rotation of the drive shaft 336 and the toothed wheel 340. The engagement between the teeth 341 of the toothed wheel 340 and the rack teeth 332 of the carriage 312 causes the carriage 312 to rotate. Drive knob 348 is rotated in one direction to advance the guide wire and in the other direction to retract the guide wire. The relationship between drive knob 350 and carriage 314 is substantially similar to that between drive knob 348 and carriage 312, and drive knob 350 is rotated in one direction to advance the pusher member and in the other direction to retract the pusher member.

In an alternative embodiment, carriages 312 and 314 can be configured to be selectively individually rotatable or jointly rotatable. For example, the drive mechanism can include a slidable drive shaft that carries both toothed wheels 340 and 342 and is slidable relative to the toothed wheels. Drive knob 348 is operatively connected to one end of the drive shaft and drive knob 350 is operatively connected to the other end of the drive shaft. The drive shaft is also slidable relative to the drive knobs 348 and 350. Additionally, the drive shaft can have spaced-a-part protrusions or bosses (ribs) that interact and engage slots 352 of toothed wheel 340 and slots 354 of toothed wheel 342 (FIG. 22). The protrusions engage slots 352 and 354 so that the toothed wheels 340 and 342 rotate when the drive shaft rotates. Similarly, the drive knobs 348 and 350 can include slots that are engaged by protrusions of the drive shaft. The protrusions of the drive shaft engage the slots of the drive knobs so that the drive shaft rotates when the drive knobs are rotated.

The carriages 312 and 314 can be selectively rotated by sliding the drive shaft into different positions. In one embodiment, the end portions of the drive shaft extend through and out of the center of the drive knobs 348 and 350 and the user can exert pressure on the end portions of the drive shaft to slide it with respect to the drive knobs 348 and 350 and toothed wheels 340 and 342. When the drive shaft is in a first position, it is engaged with the drive knob 348 and toothed wheel 340 associated with driving the guide wire and disengaged from drive knob 350 and toothed wheel 342 associated with driving the pusher member. When the drive shaft is in this position, rotation of the drive knob 348 associated with driving the guide wire rotates the drive shaft, toothed wheel 340 and carriage 312 to drive the guide wire. On the other hand, rotation of the drive knob 350 associated with driving the pusher member will not drive the drive shaft because they are disengaged. In the second position, the drive shaft engages the drive knob 350 and toothed wheel 342 associated with driving the pusher member and disengages the drive knob 348 and toothed wheel 340 associated with driving the guide wire. Thus, rotation of the drive knob 350 associated with driving the pusher member will drive the pusher member and rotation of the drive knob 348 associated with driving the guide wire does not drive the guide wire because of disengagement. Finally, in the third position, the drive shaft engages both drive knobs 348 and 350 and both toothed wheels 340 and 342. When the drive shaft is in this position, rotation of either drive knob 348 and 350 will result in driving both the guide wire and the pusher member.

An further embodiment includes a means to have a single drive knob whereby the guide wire can be advanced or retracted alone, or both the guide wire and pusher wire can be advanced or retracted together. The carriage 312 is connected to the guide wire 328 and is always in engagement with the drive knob. An axially translatable drive shaft can be manipulated in or out of engagement with the pinion gear that drives the pusher wire. Such construction may also include a lock feature that prevents movement of the pusher wire relative to the handle when the drive shaft is not engaging the pinion that drives the pusher wire. The lock is disengaged when the drive shaft is positioned to engage the pusher wire pinion. A multitude of such lock mechanisms are possible.

Referring to FIGS. 19 and 22, the drive mechanism can also include a releasable stop mechanism that can be utilized to indicated to the user to stop advancing or retracting the guide wire or the pusher member. In the embodiment shown, the stop mechanism includes recesses 356 that are located around the carriage 312 at selective intervals. The stop mechanism also includes a biased lever 358 that is partially contained within the housing 300. The lever 358 includes first end portion 360, a second end portion 362 and a middle portion there between 364. The middle portion has a hole 366 therethrough. Post 368 of the housing 300 is received within hole 366 and the lever 358 is supported by and pivotable about the post 368. The second end 362 of the lever 358 includes an arm 370 and the lever 358 is biased so that the arm 370 is urged toward the carriage 312. The lever 358 can be biased by a variety of biasing mechanisms, such as a spring. As the carriage 312 is rotated, the outer edge of the carriage contacts and passes by the arm 370 of the lever. When the arm 370 encounters a recess 356, lever 358 pivots about post 368 and the arm enters and engages the recess 356 to stop rotation of the carriage 312. To commerce further rotation of the carriage 312, the user applies pressure to the first portion 360 of the lever 358, which is preferably located exterior to the housing, to pivot the lever 358 about post 368 and remove the arm 370 from the recess 356. With the arm 370 disengaged from the recess 356, the carriage 312 can be rotated again. (Each recess can also be designed such that it locks in only one direction of carriage rotation and has a cam surface to allow free rotation in the opposite direction). It should be understood that a substantially similar stop mechanism can also be associated with carriage 314 that drives the pusher member. In addition, other lock or identifier mechanisms may be present, such as interrupted gear teeth on the carriage that prevent excess retraction. Another embodiment of a stop mechanism may include a boss on one carriage and mating annular groove on the adjacent face of the other carriage that interact to prevent undesirable rotation of one carriage relative to the other. Alternatively, another embodiment may include a stop mechanism that has male/boss features on the carriage that ride in a groove in the handle and are allowed to pass by interaction with a button. Alternatively, spring plungers could be inserted into the carriage and pop into pockets in the handle. Pressing a button would force the plunger out of engagement with the handle to release the stop mechanism.

Although the present invention is described in light of the illustrated embodiments, it is understood that this for the purposes illustration and not limitation. Other applications, modifications or use of the support or distraction device may be made without departing for the scope of this invention, as set forth in the claims now or hereafter filed.

The invention claimed is:

1. A delivery apparatus for delivering an intravertebral implant into a vertebral body of a human vertebra, the apparatus comprising:
   a housing;
   a cannula having a proximal end portion, a distal end portion and a lumen extending therebetween, said cannula including a distal end opening in communication with the lumen, the proximal end portion of the cannula operatively connected to the housing and the distal end portion of the cannula adapted for insertion into the vertebral body;
   a guide member having a proximal end portion and a distal end portion, the distal end portion of the guide member being disposable within the cannula and the proximal end portion of the guide member at least partially disposable within the housing, the guide member being advanceable relative to the intravertebral implant through the lumen of the cannula and out of the distal end opening of the cannula into the vertebral body, the guide member being configured to allow advancement of the intravertebral implant therealong so as to guide the implant through the lumen of the cannula, out of the distal end opening of the cannula and into the vertebral body;
   an advancing element having a proximal end portion and a distal end portion, the distal end portion of the advancing element disposable within the cannula and the proximal end portion of the advancing element at least partially disposable within the housing, the advancing element being advanceable relative to the guide member and contacting the intravertebral implant to advance the intravertebral implant along the guide member as the advancing element is advanced; and
   a drive system associated with the housing, the drive system including a first drive element for advancing the guide member through the lumen of the cannula and out of the distal end opening of the cannula, the drive system also including a second drive element for advancing the advancing element relative to the guide member so that the advancing element advances the implant along the guide member, and wherein the first drive element comprises a first carriage having a portion of the guide member wound thereabout, and the second drive element comprises a second carriage having a portion of the advancing element wound thereabout.

2. The delivery apparatus of claim 1 in which the drive system selectively advances the guide member and the advancing element.

3. The delivery apparatus of claim 1 in which the drive system simultaneously advances the guide member and the advancing element.

4. The delivery apparatus of claim 1 in which the advancing element is slidably connected to the guide member.

5. The delivery apparatus of claim 1 further including a flexible element operatively connecting the cannula to the housing, the flexible element having a lumen in communication with the housing and the cannula.

6. The delivery apparatus of claim 5 in which the flexible element includes a friction reducing member to reduce friction between the flexible element and the guide member.

7. The delivery apparatus of claim 6 in which the friction reducing member comprises a straightening element that selectively maintains the flexible element in a substantially linear configuration.

8. A delivery apparatus for delivering an intravertebral implant into a vertebral body of a human vertebra, comprising:
   a housing having a handle portion;
   a cannula having a proximal end portion, a distal end portion and an interior lumen extending therebetween and in communication with the housing; the cannula including a distal end opening in the distal end portion of the cannula, and the distal end portion of the cannula being adapted for insertion into the vertebral body;
   a flexible element operatively connecting the proximal end portion of the cannula to the housing, the flexible element having a lumen in communication with the housing and the cannula;
   a guide wire having a proximal end portion and a distal end portion, the distal end portion of the guide wire being disposable within the lumen of the cannula and the proximal end portion of the guide member being at least partially disposed within the housing, the distal end portion of the guide wire being advanceable relative to the intravertebral implant through the lumen of the cannula and out of the distal end opening of the cannula into the vertebral body, the distal end portion of the guide wire having a first configuration when disposed within the cannula and a second configuration when advanced out of the distal opening of the cannula and into the vertebral body, the guide wire being configured to allow advancement of the intravertebral implant along the guide wire so as to guide the implant through the lumen of the cannula, out of the distal end opening of the cannula and into a pre-selected shape within the vertebral body;
   an advancing element operatively associated with the guide wire for advancing the intravertebral implant along the guide wire; and
   a drive system disposed within the housing, wherein the drive system is configured to advance the guide wire and the advancing element.

9. The delivery apparatus of claim 8 in which the drive system includes a first drive element for advancing the guide wire, and a second drive element for advancing the advancing element.

10. The delivery apparatus of claim 9 in which the first drive element comprises a first drive shaft in contact with the guide wire, and the second drive element comprises a second drive shaft in contact with the advancing element.

11. The delivery apparatus of claim 9 in which the first drive element comprises a first carriage having a portion of the guide wire wound thereabout and the second drive element comprises a second carriage having a portion of the advancing element wound thereabout.

12. The delivery apparatus of claim 8 in which the drive system selectively advances the guide wire and the advancing element.

13. The delivery apparatus of claim 8 in which the drive system simultaneously advances the guide wire and the advancing element.

14. The delivery apparatus of claim 8 wherein the second configuration is a predefined configuration and the distal end portion of the guide wire changes from the first configuration to the second predefined configuration as the guide wire is advanced out of the distal opening of the cannula and into the vertebral body.

15. The delivery apparatus of claim 8 in which the flexible element includes a friction reducing member to reduce friction between the flexible element and the guide wire.

16. The delivery apparatus of claim 15 in which the friction reducing member comprises a straightening element that selectively maintains the flexible element in a substantially linear configuration.

17. A delivery apparatus for delivering an intravertebral implant into a vertebral body of a human vertebra, the apparatus comprising:
   a housing;
   a cannula having a proximal end portion, a distal end portion and a lumen extending therebetween, said cannula including a distal end opening in communication with the lumen, a flexible element operatively connecting the proximal end portion of the cannula to the housing, the flexible element having a lumen in communication with the housing and the cannula, and the distal end portion of the cannula adapted for insertion into the vertebral body;
   a guide member having a proximal end portion and a distal end portion, the distal end portion of the guide member being disposable within the cannula and the proximal end portion of the guide member at least partially disposable within the housing, the guide member being advanceable through the lumen of the cannula and out of the distal end opening of the cannula into the vertebral body, the guide member being configured to allow advancement of the intravertebral implant along the guide member so as to guide the implant through the lumen of the cannula, out of the distal end opening of the cannula and into the vertebral body;
   an advancing element having a proximal end portion and a distal end portion, the distal end portion of the advancing element disposable within the cannula and the proximal end portion of the advancing element at least partially disposable within the housing, the advancing element being advanceable relative to the guide member and contacting the intravertebral implant to advance the intravertebral implant along the guide member as the advancing element is advanced; and
   a drive system associated with the housing, the drive system configured to advance the guide member through the lumen of the cannula and out of the distal end opening of the cannula, the drive system also configured to advance the advancing element relative to the guide member so that the advancing element advances the implant along the guide member.

18. The delivery apparatus of claim 17 in which the flexible element includes a friction reducing member to reduce friction between the flexible element and the guide member.

19. The delivery apparatus of claim 18 in which the friction reducing member comprises a straightening element that selectively maintains the flexible element in a substantially linear configuration.

20. The delivery apparatus of claim 17 in which the drive system includes a first drive element for advancing the guide member and a second drive element for advancing the advancing element.

21. The delivery apparatus of claim 20 in which the first drive element comprises a first drive shaft in contact with the guide member, and the second drive element comprises a second drive shaft in contact with the advancing element.

22. The delivery apparatus of claim 17 in which the drive system selectively advances the guide member and the advancing element.

23. The delivery apparatus of claim 17 in which the drive system simultaneously advances the guide member and the advancing element.

24. The delivery apparatus of claim 17 in which the advancing element is slidably connected to the guide member.

\* \* \* \* \*